US005604219A

United States Patent [19]
Murakata et al.

[11] Patent Number: 5,604,219
[45] Date of Patent: Feb. 18, 1997

[54] INDOLOCARBAZOLE DERIVATIVES THAT STIMULATE PLATELET PRODUCTION

[75] Inventors: Chikara Murakata, Hachioji; Junichi Watanabe, Sunto-gun; Yutaka Saitoh, Machida; Yukimasa Shiotsu, Tokyo; Takako Shiraki, Machida; Fumihiko Kanai, Machida; Tatsuya Tamaoki, Machida; Shiro Akinaga, Sunto-gun; Masami Okabe, Mishima, all of Japan

[73] Assignee: Kyowa Hakko Kogyo Co., Ltd., Tokyo, Japan

[21] Appl. No.: 404,961

[22] Filed: Mar. 16, 1995

[30] Foreign Application Priority Data

Mar. 18, 1994 [JP] Japan .................... 6-049578

[51] Int. Cl.$^6$ .......................... A61K 31/55; C07D 498/22
[52] U.S. Cl. ........................... 514/211; 540/545
[58] Field of Search ..................... 540/546, 544, 540/545; 514/211

[56] References Cited

U.S. PATENT DOCUMENTS

| 4,923,986 | 5/1990 | Murakata et al. | 540/545 |
| 5,093,330 | 3/1992 | Caravatti et al. | 540/545 |
| 5,344,926 | 9/1994 | Murakata et al. | 540/546 |
| 5,455,241 | 10/1995 | Wacker | 540/545 |

FOREIGN PATENT DOCUMENTS

| 0575955 | 12/1993 | European Pat. Off. . |
| 0630898 | 12/1994 | European Pat. Off. . |

OTHER PUBLICATIONS

Chemical Abstracts, vol. 115, No. 9 (Sep. 1991) p. 808 (92688z).
Hidaka et al., Ann. Rev. Pharmacol. Toxicol., vol. 32 (1992) 377:97.

Primary Examiner—Mukund J. Shah
Assistant Examiner—Pavanaram K. Sripada
Attorney, Agent, or Firm—Fitzpatrick, Cella, Harper & Scinto

[57] ABSTRACT

Disclosed is an indolocarbazole derivative represented by the following formula (I), or a pharmaceutically acceptable salt thereof:

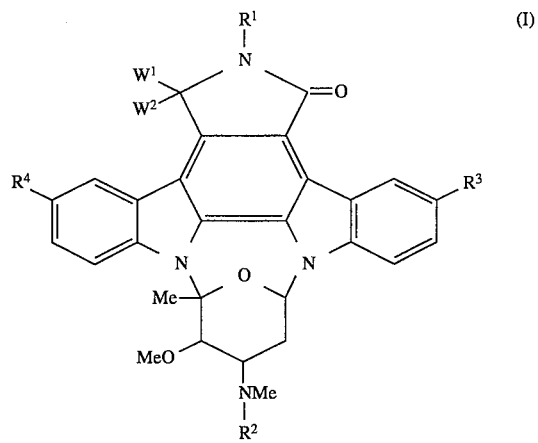

[wherein $R^1$ represents substituted or unsubstituted lower alkyl, $R^2$ represents hydrogen, substituted or unsubstituted lower alkyl, $R^3$ and $R^4$ are the same or different, and represent hydrogen, nitro, $NR^5R^6$, $OR^9$, substituted or unsubstituted lower alkyl, substituted or unsubstituted lower alkenyl, or $CH=NNR^{10}R^{11}$, W represents two hydrogen atoms or oxygen, and Me represents methyl, provided that when $R^1$ is unsubstituted lower alkyl, $R^3$ and $R^4$ are not simultaneously hydrogen.

11 Claims, No Drawings

INDOLOCARBAZOLE DERIVATIVES THAT STIMULATE PLATELET PRODUCTION

BACKGROUND OF THE INVENTION

The present invention relates to a novel indolocarbazole derivative or a pharmaceutically acceptable salt thereof. These compounds are expected to be useful as a therapeutic agent for thrombocytopenia.

The decrease in the number of blood platelets due to various kinds of hematopoietic disorders causes grave symptoms including an increased tendency to hemorrhage. At present, platelet transfusion is effective against such decreases. However, a sufficient amount of blood platelets is not always supplied. In addition to platelet transfusion, interleukin (IL) 6 and IL 11, which are hematopoietic factors that stimulate the production of blood platelets are known [Blood, 75, 1602 (1990); Blood, 81, 901 (1993)].

Indolocarbazole derivatives having staurosporine skeleton are known to have protein kinase C inhibitory activity, anti-tumor activity and antibacterial activity [WO89/07105, WO92/17181, Japanese Published Unexamined Patent Application No. 220196/87, Japanese Published Unexamined Patent Application No. 86068/93], platelet aggregation inhibitory activity [Japanese Published Unexamined Patent Application No. 72485/91, Japanese Published Unexamined Patent Application No. 163325/91, Japanese Published Unexamined Patent Application No. 220194/91, Japanese Published Unexamined Patent Application No. 145085/92, Japanese Published Unexamined Patent Application No. 364186/92], vasodilating activity [Japanese Published Unexamined Patent Application No. 143877/89, Japanese Published Unexamined Patent Application No. 9819/90], antiobestic activity [WO89/11295] or macrophage activating activity [Journal of Antibiotics, 42, 1619 (1989)] and so on.

However, it is not known that indolocarbazole derivatives have an activity to stimulate the production of blood platelets.

Most of the known indolocarbazole derivatives have hydrogen at the position corresponding to $R^1$ in the following formula (I). Alternatively, the known indolocarbazole derivatives have lower alkyl at the position corresponding to $R^1$, and hydrogen at the positions corresponding to $R^3$ and $R^4$ in the following formula (I).

SUMMARY OF THE INVENTION

It is an object of the invention to provide a novel indolocarbazole derivative or a pharmaceutically acceptable salt thereof, which is useful as a therapeutic agent for thrombocytopenia.

The present invention relates to an indolocarbazole derivative represented by the formula (I):

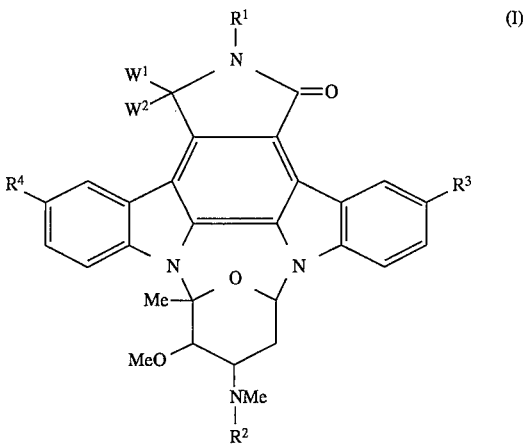

[wherein $R^1$ represents substituted or unsubstituted lower alkyl, $R^2$ represents hydrogen, substituted or unsubstituted lower alkyl, $R^3$ and $R^4$ are the same or different, and represent hydrogen, nitro, $NR^5R^6$ [wherein $R^5$ and $R^6$ are the same or different and represent hydrogen, lower alkyl, an amino acid residue where hydroxy group in the carboxylic acid is removed from the amino acid, alkanoyl or $CO(CH_2)_m NR^7R^8$ (wherein m is an integer of 0 to 3, $R^7$ and $R^8$ are the same or different and represent hydrogen or lower alkyl, or $R^7$ and $R^8$ are combined together with nitrogen atom to form a heterocyclic ring)], $OR^9$ [wherein $R^9$ represents long-chained alkyl, alkanoyl, $COCH_2(OCH_2CH_2)_k OCH_3$ (wherein k is an integer of 1 to 6), or $CONR^7R^8$ (wherein $R^7$ and $R^8$ have the same meanings as defined above)], substituted or unsubstituted lower alkyl, substituted or unsubstituted lower alkenyl, or $CH=NNR^{10}R^{11}$ (wherein $R^{10}$ and $R^{11}$ are the same or different and represent hydrogen, lower alkyl or a heterocyclic ring containing nitrogen atom), $W^1$ and $W^2$ are both hydrogen or are combined together to represent oxygen, and Me represents methyl, provided that when $R^1$ is unsubstituted lower alkyl, $R^3$ and $R^4$ are not simultaneously hydrogen], or a pharmaceutically acceptable salt thereof.

The compound represented by the formula (I) is hereinafter referred to as to Compound (I). The same numbering applies to the compounds having other formula numbers.

DETAILED DESCRIPTION OF THE INVENTION

The substituted or unsubstituted lower alkyl means a straight or branched alkyl having 1–6 carbon atoms such as methyl, ethyl, propyl, isopropyl, butyl, isobutyl, secbutyl, tert-butyl, pentyl, neopentyl and hexyl, which is optionally substituted with 1 to 3 substituents independently selected from the group consisting of lower alkoxycarbonyl, $OR^{12}$ [wherein $R^{12}$ represents hydrogen, or lower alkyl which may be substituted by $NR^{7a}R^{8a}$ (wherein $R^{7a}$ and $R^{8a}$ have the same meanings as those defined for above-mentioned $R^7$ and $R^8$)], and $SR^{13}$ [wherein, $R^{13}$ represents hydrogen, heteroaryl group or lower alkyl which may be substituted by $NR^{7b}R^{8b}$ (wherein, $R^{7b}$ and $R^{8b}$ have the same meanings as those defined for the above-mentioned $R^7$ and $R^8$)]. The alkyl moiety in the lower alkoxycarbonyl, and the alkyl in the definitions of $R^{12}$ and $R^{13}$ have the same definition as the lower alkyl mentioned above. The heteroaryl represents pyrrolyl, imidazolyl, thienyl, furyl, triazolyl, tetrazolyl, thiazolyl, oxazolyl, pyridyl, pyrimidinyl, indolyl, quinolyl, and the like. The long-chained alkyl means a linear or branched alkyl having 7–20 carbon atoms such as heptyl, octyl, isooctyl, nonyl, isononyl, pentadecanyl and eicosyl and the like.

The substituted or unsubstituted lower alkenyl means an alkenyl having 2–6 carbon atoms such as vinyl, allyl, butenyl pentenyl, hexenyl, pentadienyl, hexadienyl and the like, which is optionally substituted with 1 to 2 of the same substituents as those for the substituent in the lower alkyl mentioned above.

Alkanoyl means a straight or branched alkanoyl having 1–20 carbon atoms, such as formyl, acetyl, propionyl, isopropionyl, butyryl, valeryl, pivaloyl, hexanoyl, octanoyl, nonanoyl, palmitoyl, stearoyl and the like.

Amino acid means glycine, alanine, serine, cysteine, lysine, glutamic acid, phenylalanine, proline and the like.

The heterocyclic group formed together with nitrogen atom and the heterocyclic group containing nitrogen atom are the same or different and include pyrrolidinyl, pyrrolinyl, imidazolidinyl, imidazolinyl, pyrazolidinyl, pyrazolinyl, piperidyl, piperazinyl, morpholinyl, thiomorpholinyl, N-methylpiperazinyl, indolinyl, isoindolinyl and the like.

In Compound (I), $R^1$ preferably represents unsubstituted alkyl, more preferably methyl. $R^2$ preferably represents hydrogen. $R^3$ and $R^4$ preferably represents $NR^5R^6$ (wherein $R^5$ and $R^6$ have the same meanings as defined above), $OR^9$ (wherein $R^9$ has the same meaning as defined above), substituted or unsubstituted lower alkyl, substituted or unsubstituted lower alkenyl, or $CH=NNR^{10}R^{11}$ (wherein $R^{10}$ and $R^{11}$ have the same meanings as defined above). W preferably represents two hydrogen atoms.

The pharmaceutically acceptable salts of Compound (I) include pharmaceutically acceptable acid addition salts, which include salts with inorganic acids such as hydrochloride, sulfate, and phosphate, and salts with organic acids such as acetate, maleate, fumarate, tartrate, citrate, lactate, aspartate and glutamate.

The compounds of the present invention are normally obtained from optically active staurosporine as a starting material [Journal of Antibiotics, 30, 275 (1977)]. The present invention covers all the possible stereoisomers and a mixture thereof.

The processes for the production of Compound (I) are described below.

In the following production processes, when the defined group changes under the condition of the process employed, or is inappropriate for carrying out the process, typical protection and deprotection processes of the organic synthetic chemistry can be used to obtain the desired compound [see, e.g. T. W.Greene, Protective Groups in Organic Synthesis, John Wiley & Sons Inc. (1981)]. It is also possible to change the order of the substituent introduction steps if necessary.

In the formulae and in the tables, Me, Et, t-Bu and Ac stand for methyl, ethyl, t-butyl and acetyl groups, respectively.

Production process 1

Compound (IA) [Compound (I) in which a substituent is introduced at $R^1$ position] can be produced according to the following step.

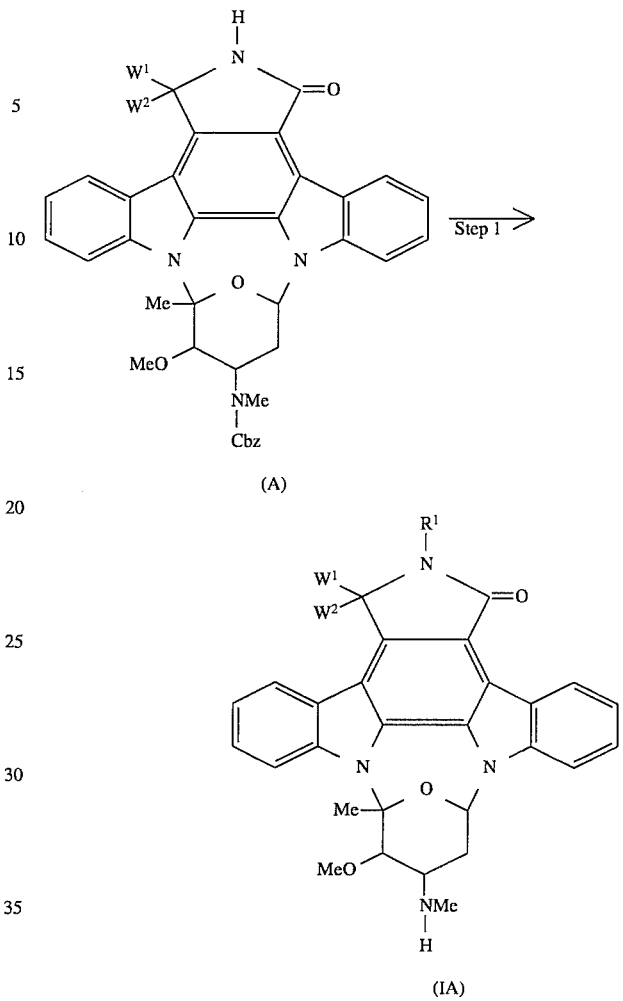

(In the formulae, $R^1$, $W^1$ and $W^2$ have the same meanings as defined above, and Cbz represents benzyloxycarbonyl.)

Step 1

Compound (A) which is obtained by a known method (WO89-07105) from staurosporine [Journal of Antibiotics, 30, 275 (1977)] is allowed to react with Compound (II) which is represented by the following formula (II):

$R^1Hal$ (II)

(wherein, $R^1$ has the same definition as defined above, Hal represents chloride, bromide or iodide), in the presence of a base in a solvent which is inert to the reaction, and then the protecting group Cbz is removed to give Compound (IA).

N,N-dimethylformamide (DMF), tetrahydrofuran (THF), toluene and the like can be used alone or in combination as a reaction solvent, and sodium hydroxide, potassium tert-butoxide and the like can be used as a base. The reaction is carried out at −20° to 50° C. and is completed in 1 to 24 hours.

The protecting group Cbz is removed by catalytic reduction in a solvent such as DMF and THF in the presence of a catalyst such as 10% Pd/C and 20% Pd(OH)$_2$/C in a hydrogen stream to give Compound (IA). The amount of the reducing catalyst to be used is 10–100% (by weight) based on CBz-protected derivative. The reaction is carried out at −10° to 50° C. and is completed in 1 to 24 hours.

Production process 2

Compound (IB) [Compound (I) in which a substituent is introduced at the $R^2$ position] can be produced according to the following steps, from Compound (IA) which is obtained by the production process 1.

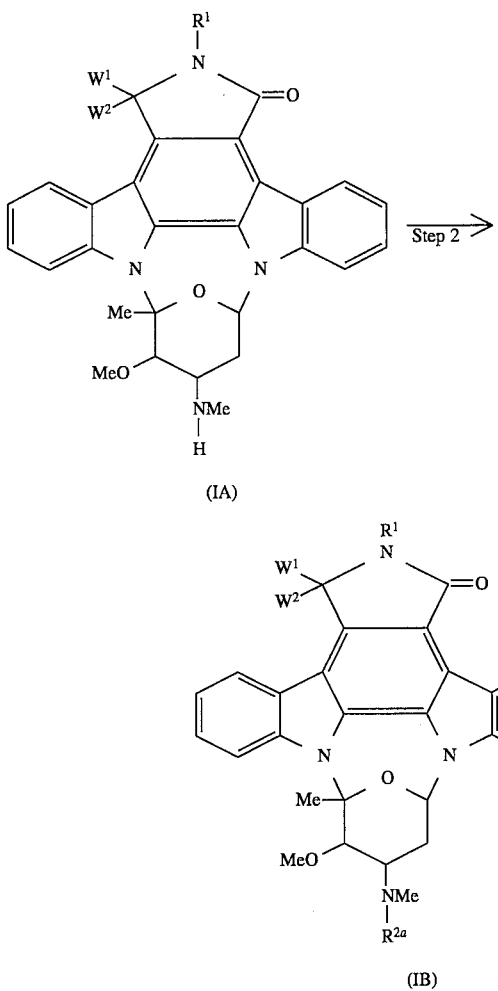

(IA)

(IB)

(In the formulae, $R^{2a}$ represents all the groups but hydrogen in the definition of $R^2$, and $R^1$, $W^1$ and $W^2$ have the same meanings as defined above.)

Step 2

Compound (IA) is allowed to react with Compound (III) which is represented by the following formula (III):

$$R^{14}CHO \qquad (III)$$

(wherein, $R^{14}$ represents substituted or unsubstituted alkyl having the number of carbon atoms which is less by one than that of the lower alkyl in the definition of the above-defined $R^2$), or a dimer thereof, in the presence of a reducing agent such as sodium cyanoborohydride in a solvent such as a mixture of THF and water (10/1), at pH 5 to 6 to give Compound (IB). Sodium cyanoborohydride, Compound (III) or the dimer thereof are used in amounts of 1 to 1.5 equivalents, respectively, based on Compound (IA). The reaction is carried out at −10° to 50° C. and is completed in 1 to 8 hours.

Production process 3

Compound (IC) [Compound (I) in which a substituent is introduced at $R^3$ and/or $R^4$ positions] can be produced according to the following steps or according to the process described in WO88/07045, from Compound (B) which is obtained by Production process 1 or Production process 2.

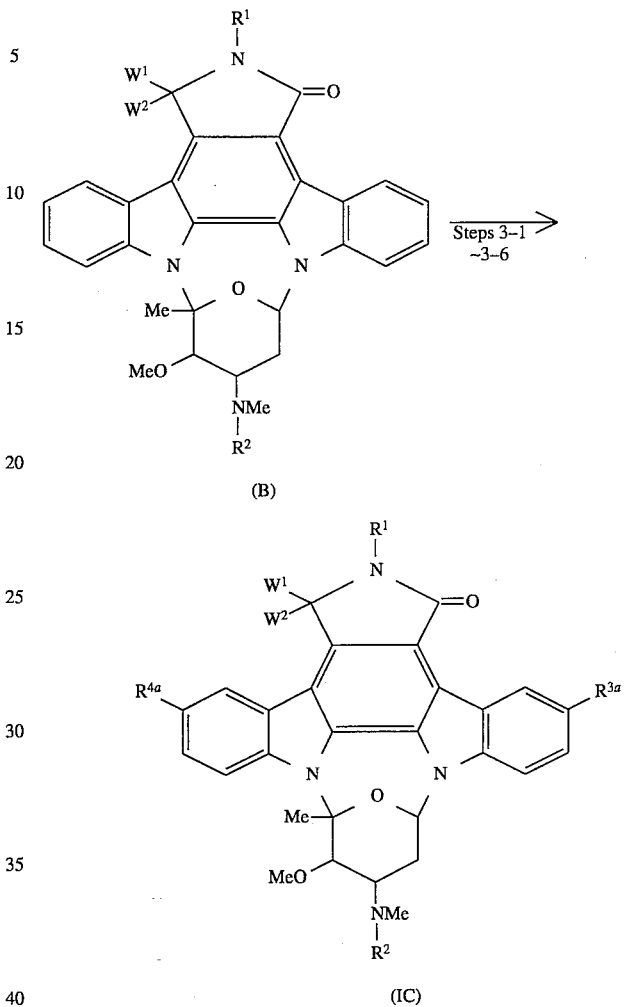

(B)

(IC)

(Wherein $R^1$, $R^2$, $W^1$ and $W^2$ have the same meanings as defined above, and the definitions of $R^{3a}$ and $R^{4a}$ are given in the following steps.)

Step 3-1

(In the formulae, at least one of $R^{3a}$ and $R^{4a}$ is nitro.)

Compound (B) is allowed to react with fuming nitric acid in the presence of trifluorosulfonic acid in a solvent such as dichloromethane to give Compound (IC). Trifluorosulfonic acid and fuming nitric acid are used in amounts of 1 to 3 equivalents, respectively, based on Compound (B). The reaction is carried out at −78° to 30° C. and is completed in 1 to 8 hours.

Step 3-2

(In the formulae, at least one of $R^{3a}$ and $R^{4a}$ is hydroxymethyl.)

Compound (B) is allowed to react with dichloromethyl methyl ether in the presence of a Lewis acid such as titanium tetrachloride in a solvent such as methylene chloride, chloroform, and dichloroethane to give formyl derivative which is a compound wherein at least one of $R^{3a}$ and $R^{4a}$ is formyl. Titanium tetrachloride and dichloromethyl methyl ether are used in amounts of 1 to 10 equivalents, respectively, based on Compound (B). The reaction is carried out at −10° to 80° C. and is completed in 1 to 8 hours.

The resulting formyl derivative is allowed to react with a reducing agent such as sodium borohydride in a solvent such as a mixed solvent of THF and methanol (1/1) to give Compound (1C). The sodium borohydride is used in an amount of 1 to 5 equivalents based on the formyl derivative. The reaction is carried out at −10° to 50° C. and is completed in 1 to 8 hours.

Step 3-3

(In the formulae, at least one of $R^{3a}$ and $R^{4a}$ is substituted or unsubstituted lower alkenyl.)

The formyl derivative obtained as a reaction intermediate in the above-mentioned step 3-2 is allowed to react with a corresponding Wittig's reagent in a solvent such as dichloroethane to give Compound (IC). Wittig's reagent is used in an amount of 1 to 3 equivalents, based on the formyl derivative. The reaction is carried out at 0° to 80° C. and is completed in 5 to 24 hours.

Step 3-4

(In the formulae, at least one of $R^{3a}$ and $R^{4a}$ is alkanoyloxy or $COCH_2(OCH_2CH_2)_kOCH_3$ (wherein k has the same meaning as defined above)).

The formyl derivative obtained as a reaction intermediate in the above-mentioned step 3-2 is allowed to react with a peroxide such as m-chloroperbenzoic acid in the presence of a base such as sodium hydrogen carbonate in a solvent such as dichloromethane and chloroform to give formic ester. The peroxide and the base are used in amounts of 1–5 equivalents, and 3 to 10 equivalents, respectively, based on the formic ester. The reaction is carried out at −10° to 50° C. and is completed in 1 to 24 hours.

Then the obtained formic ester is allowed to react with a base such as sodium methoxide, in a solvent such as dichloromethane to give hydroxy derivative. Sodium methoxide is used in an amount of 1 to 5 equivalents, based on the formic ester. The reaction is carried out at −10° to 50° C. and is completed in 10 minutes to 1 hour.

Then the above-mentioned hydroxy derivative is allowed to react with an acid halide such as chloride and bromide of a corresponding carboxylic acid in the presence of a base such as triethylamine in a solvent such as dichloromethane to give Compound (IC). The acid halide and the base are used in amounts of 1 to 3 equivalents, respectively, based on the hydroxy derivative. The reaction is carried out at 0° to 30° C. and is completed in 0.5 to 5 hours.

Step 3-5

[In the formulae, at least one of $R^{3a}$ and $R^{4a}$ is $OCONR^7R^8$ (wherein, $R^7$ and $R^8$ have the same meanings as defined above.)]

The hydroxy derivative obtained as a reaction intermediate in the above-mentioned step 3-4 is allowed to react with 4-nitrophenyl chloroformate in the presence of triethylamine in a solvent such as dichloromethane to give 4-nitrophenyl carbonate. 4-Nitrophenyl chloroformate and the base are used in amounts of 1 to 3 equivalents, respectively, based on the hydroxy derivative. The reaction is carried out at 0° to 30° C. and is completed in 0.5 to 5 hours.

Then the obtained carbonate is allowed to react with Compound (IV) which is represented by the following formula:

$$R^7R^8NH \quad (IV)$$

(wherein $R^7$ and $R^8$ have the same meanings as defined above), in the presence of a base such as triethylamine and diisopropylethylamine in a solvent such as chloroform to give Compound (IC). Compound (IV) and the base are used in amounts of 1 to 10 equivalents, respectively, based on the carbonate. The reaction is carried out at 0° to 50° C. and is completed in 1 to 24 hours.

Step 3-6

[In the formulae, at least one of $R^{3a}$ and $R^{4a}$ is long-chained alkyl (wherein the long-chained alkyl has the same meanings as defined above.)]

The hydroxy derivative obtained as a reaction intermediate in the above-mentioned step 3-4 is allowed to react with alkyl halide (wherein the halogen is chloride, bromide or iodide) in the presence of a base such as sodium hydride in a solvent such as DMF to give Compound (IC). Alkyl halide and the base are used in amounts of 1 to 5 equivalents, respectively, based on the hydroxy derivative. The reaction is carried out at −23° to 30° C. and is completed in 1 to 8 hours.

Production process 4

Compounds having various substituents at $R^3$ and/or $R^4$ positions can also be produced according to the following steps.

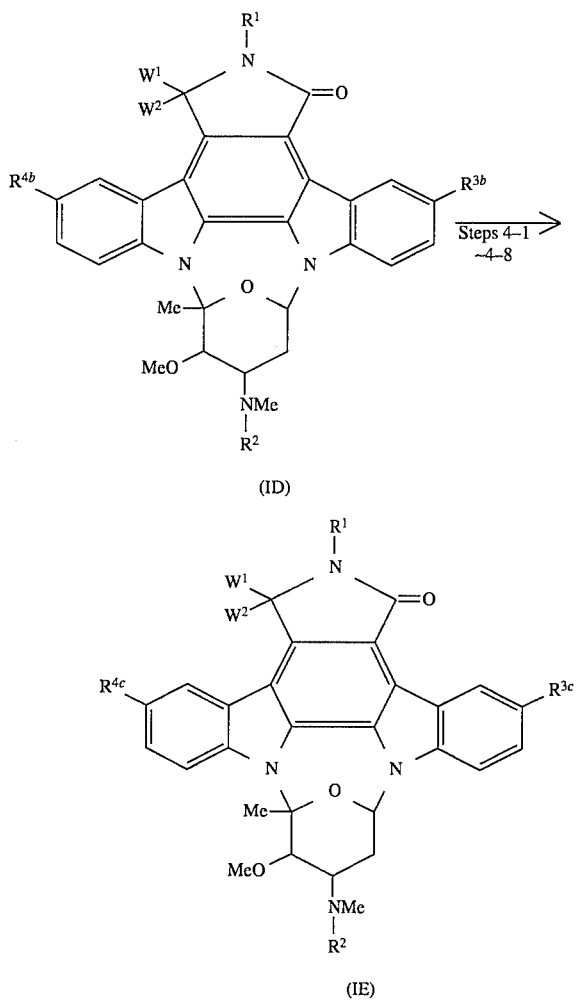

(Wherein $R^1$, $R^2$, $W^1$ and $W^2$ have the same meanings as defined above, and the definitions of $R^{3b}$ and $R^{4b}$, and $R^{3c}$ and $R^{4c}$ are given in the following steps.)

Step 4-1

(In the formulae, at least one of $R^{3b}$ and $R^{4b}$ is nitro, and at least one of $R^{3c}$ and $R^{4c}$ is amino.)

Compound (ID) is reduced in a solvent such as DMF, in the presence of 10% Pd/C under a hydrogen atmosphere to give Compound (IE). 10% Pd/C is used in an amount of 10–200% (by weight) based on Compound (ID). The reaction is carried out at 0° to 50° C. and is completed in 1 to 5 hours.

Step 4-2

[In the formulae, at least one of $R^{3b}$ and $R^{4b}$ is amino, and at least one of $R^{3c}$ and $R^{4c}$ is $NR^{5a}R^{6a}$ (wherein $R^{5a}$ and $R^{6a}$ are the same or different and represent lower alkyl having the same definitions as above)].

Compound (ID) is allowed to react with Compound (V) which is represented by the following formula:

$$R^{15}CHO \qquad (V)$$

(wherein, $R^{15}$ represent alkyl having the number of carbon atoms which is less by one than that of the lower alkyl in the above-defined $R^{5a}$ and $R^{6a}$), or a dimer thereof, in the presence of a reducing agent such as sodium cyanoborohydride in a solvent such as a mixture of THF with water (10/1) at pH 5–6 to give Compound (IE). Sodium cyanoborohydride, Compound (V) and the dimer thereof are used in amounts of 1 to 1.5 equivalents, respectively, based on Compound (ID). The reaction is carried out at −10° to 50° C. and is completed in 1 to 8 hours.

Step 4-3

[In the formulae, at least one of $R^{3b}$ and $R^{4b}$ is amino, and at least one of $R^{3c}$ and $R^{4c}$ is $NHR^{5b}$ (wherein $R^{5b}$ is an amino acid residue where hydroxy group in the carboxylic acid is removed from the amino acid)].

Compound (ID) is allowed to react with an amino acid in the presence of a condensation agent such as 1-ethyl-3-(3-dimethylaminopropyl)-carbodiimide in a solvent such as dichloromethane to give Compound (IE). The condensing agent and the amino acid are used in amounts of 1 to 3 equivalents, respectively, based on Compound (ID). The reaction is carried out at −10° to 50° C. and is completed in 1 to 24 hours. The amino acid to be used is one whose amino group is protected by benzyloxycarbonyl group, t-butyloxycarbonyl group and the like. After completion of the reaction, deprotection is carried out by a conventional process such as catalytic reduction, treatment with an acid and the like.

Step 4-4

[In the formulae, at least one $R^{3b}$ and $R^{4b}$ is amino, and at least one $R^{3c}$ and $R^{4c}$ is $NHCONHR^{7a}$ (wherein, $R^{7a}$ is a lower alkyl having the same meaning as defined above)].

Compound (ID) is allowed to react with Compound (VI) which is represented by the following formula:

$$R^{7a}NCO \qquad (VI)$$

(wherein $R^{7a}$ has the same meaning as defined above) in a solvent such as dichloromethane to give Compound (IE). Compound (VI) is used in an amount of 1 to 10 equivalents based on Compound (ID). The reaction is carried out at 0° to 100° C. and is completed in 1 to 5 hours.

Step 4-5

[In the formulae, at least one of $R^{3b}$ and $R^{4b}$ is amino, and at least one of $R^{3c}$ and $R^{4c}$ is $NHCO(CH_2)_mNR^7R^8$ (wherein $R^7$, $R^8$ and m have the same meanings as defined above.)]

Compound (ID) is allowed to react with Compound (VII) which is represented by the following formula (VII):

$$Hal^1\text{-}(CH_2)_mCO\text{—}Hal^2 \qquad (VII)$$

(wherein $Hal^1$ and $Hal^2$ are the same or different, and have the same meanings as defined for the above-mentioned Hal, and m has the same meaning as defined above) in the presence of a base such as triethylamine in a solvent such as dichloromethane to give amide derivative. Compound (VII) and the base are used in amounts of 1 to 3 equivalents, respectively, based on Compound (ID). The reaction is carried out at 0° to 30° C. and is completed in 0.5 to 5 hours.

Then the amide is allowed to react with Compound (IV) in the presence of a base such as triethylamine and diisopropylethylamine in a solvent such as chloroform to give Compound (IE). Compound (IV) and the base are used in amounts of 1–10 equivalents, respectively, based on the amide derivative. The reaction is carried out at 20° to 100° C. and is completed in 1 to 24 hours.

Step 4-6

[In the formulae, at least one of $R^{3b}$ and $R^{4b}$ is hydroxymethyl, and at least one of $R^{3c}$ and $R^{4c}$ is $CH_2OR^{12a}$ (wherein $R^{12a}$ represents all the groups but hydrogen in the definition of $R^{12}$) or $CH_2SR^{13a}$ (wherein $R^{13a}$ represents all the groups but hydrogen in the definition of $R^{13}$)].

Compound (ID) is allowed to react with Compound (VIII) or Compound (IX) which is represented by the following formula (VIII) or (IX);

$$R^{12a}OH \qquad (VIII)$$

or $$R^{13a}SH \qquad (IX),$$

(wherein $R^{12}$ and $R^{13}$ have the same meanings defined as above) in the presence of camphorsulfonic acid in a solvent such as chloroform to give Compound (IE). Camphorsulfonic acid is used in an amount of 1 to 20 equivalents, and Compound (VIII) or Compound (IX) is used in an amount of 5 to 20 equivalents, respectively, based on Compound (ID). The reaction is carried out at 0° to 50° C. and is completed in 1 to 24 hours.

Step 4-7

(In the formulae, at least one of $R^{3b}$ and $R^{4b}$ is substituted or unsubstituted lower alkenyl, and at least one of $R^{3c}$ and $R^{4c}$ is substituted or unsubstituted lower alkyl.)

Compound (ID) is hydrogenated in a solvent such as a mixture of DMF and acetic acid (2/1), in the presence of 20% $Pd(OH)_2/C$ under a hydrogen atmosphere, to give Compound (IE). 20% $Pd(OH)_2/C$ is used in an amount of 10–200% (by weight) based on Compound (ID). The reaction is carried out at 0° to 50° C. and is completed in 1 to 5 hours.

Step 4-8

(In the formulae, at least one of $R^{3b}$ and $R^{4b}$ is lower alkyl substituted with hydroxy, and at least one of $R^{3c}$ and $R^{4c}$ is lower alkyl.)

Compound (ID) is allowed to react with triethylsilane in the presence of trifluoroacetic acid in a solvent such as dichloromethane to give Compound (IE). Trifluoroacetic acid is used in an amount of 10 to 100 equivalents and triethylsilane is used in an amount of 3 to 10 equivalents, based on Compound (ID). The reaction is carried out at 0° to 50° C. and is completed in 10 minutes to 8 hours.

Production process 5

Compound (IG) [Compound (I) in which $R^1$ is hydroxy-substituted lower alkyl]can be produced not only according to the Production process 1 but also according to the following steps.

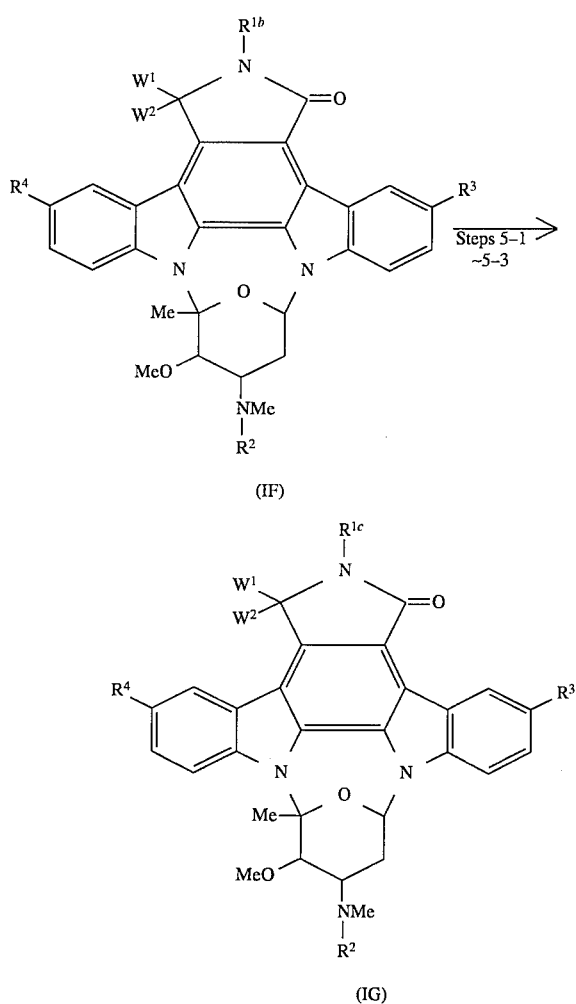

(wherein, $R^2$, $R^3$, $R^4$, $W^1$ and $W^2$ have the same meanings as defined above, and the definitions of $R^{1b}$ and $R^{1c}$ are given in the following steps.)

Step 5-1

[In the formulae, $R^{1b}$ is —$(CH_2)_nCH=CH_2$ (wherein n is an integer of 0–4), and $R^{1c}$ is —$(CH_2)_nCH(OH)CH_2OH$ (wherein n has the same meaning as defined above].

Compound (IF) obtained according to a process similar to Production process 1 is allowed to react with osmium tetroxide in a solvent such as a mixture of chloroform and acetone (1/1) in the presence of N-methylmorpholine N-oxide to give Compound (IG). Osmium tetroxide is used in an amount of 0.02 to 1 equivalent, and N-methyl morpholine N-oxide is used in an amount of 1 to 5 equivalents based on Compound (IF). The reaction is carried out at −10° to 50° C. and is completed in 1 to 8 hours.

Step 5-2

[In the formulae, $R^{1b}$ is —$(CH_2)_nCH=CH_2$ (wherein n has the same meaning as defined above) and $R^{1c}$ is —$(CH_2)_nCH_2CH_2OH$ or —$(CH_2)_nCH(OH)CH_3$ (wherein n has the same meaning defined as above)].

Compound (IF) is allowed to react with a reducing agent such as borane-THF complex in a solvent such as THF, and treated with 30% aqueous hydrogen peroxide in the presence of 3M sodium hydroxide to give Compound (IG). The borane-THF complex is used in an amount of 0.5 to 1.5 equivalents based on Compound (IF) and 3M sodium hydroxide and 30% aqueous hydrogen peroxide are used in amounts of 0.1 to 1 ml, respectively, based on 1 mmol of Compound (IF). The reaction is carried out at −10° to 50° C. and is completed in 1 to 8 hours.

Step 5-3

[In the formulae, $R^{1b}$ is —$(CH_2)_nCH(OH)CH_2OH$ (wherein n has the same meaning as defined above) and $R^{1c}$ is —$(CH_2)_nCH_2OH$ (wherein n has the same meaning as defined above)].

Compound (IF) is allowed to react with an oxidizing agent such as sodium periodate in a solvent such as a mixture of THE and water (5/3) to give formyl derivative wherein $R^{1b}$ is converted to —$(CH_2)_nCHO$. The obtained formyl derivative is allowed to react with a reducing agent such as sodium borohydride in an appropriate solvent such as a mixture of THF and methanol (1/1) to give Compound (IG). The sodium periodate is used in an amount of 1 to 3 equivalents based on Compound (IF). The reaction is carried out at −10° to 50° C. and is completed in 1 to 8 hours.

A functional group contained in $R^1$, $R^2$, $R^3$ or $R^4$ can be also changed by other known processes in addition to the above processes [for example, R. C. Larock, Comprehensive Organic Transformations (1989)].

Isolation and purification of the products in the above processes can be carried out using an appropriate combination of methods conventionally used in organic synthesis, for example, filtration, extraction, washing, drying, concentration, crystallization and various types of chromatography. The reaction intermediate can be used in the subsequent reaction without purification.

In the case where a salt of Compound (I) is desired, and it is produced in the form of the desired salt, it can be subjected to purification as such. In the case where Compound (I) is produced in the free state and its salt is desired, Compound (I) is dissolved or suspended in a suitable solvent, followed by addition of an acid to form a salt.

Compound (I) or a pharmaceutically acceptable salt thereof may also exist in the form of an adduct with water or various solvents. These adducts are within the scope of the present invention.

Examples of Compound (I) are listed in Table 1.

TABLE 1

[Structure diagram showing a polycyclic compound with substituents R¹ (on N), W¹, W² (on carbon), R³ and R⁴ (on the two benzene rings), R² (on NMe below), and a ring containing Me, MeO, NMe-R² substituents]

| Compd. | W¹,W² | R¹ | R² | R³ | R⁴ | Salt |
|---|---|---|---|---|---|---|
| 1 | H,H | $CH_2OH$ | H | H | H | |
| 2 | H,H | $CH_2CH(OH)CH_2OH$ | H | H | H | HCl |
| 3 | H,H | $(CH_2)_2OH$ | H | H | H | |
| 4 | H,H | $(CH_2)_3OH$ | H | H | H | |
| 5 | H,H | $CH_2CH(OH)CH_3$ | H | H | H | |
| 6 | H,H | Me | H | $CH_2OH$ | H | |
| 7 | H,H | Me | H | $CH_2OH$ | $CH_2OH$ | |
| 8 | H,H | Me | H | Me | H | |
| 9 | H,H | Me | H | Me | Me | HCl |
| 10 | H,H | Me | H | Et | Et | HCl |
| 11 | H,H | Me | H | —CH=CH—$CO_2Et$ | H | |
| 12 | H,H | Me | H | $NH_2$ | H | 2HCl |
| 13 | H,H | Me | H | $NMe_2$ | H | 2HCl |
| 14 | H,H | Me | H | —NH—C(O)—$CH_2NH_2$ (N-Me) | H | 2HCl |
| 15 | H,H | Me | H | —N(Me)—C(O)—$CH_2$—N(piperazine)—N—Me | H | 3HCl |
| 16 | H,H | Me | H | $NH_2$ | $NH_2$ | 3HCl |
| 17 | H,H | Me | H | $NMe_2$ | $NMe_2$ | 3HCl |
| 18 | H,H | Me | H | —N(Me)—C(O)—$CH_2NH_2$ | —N(Me)—C(O)—$CH_2NH_2$ | 3HCl |
| 19 | H,H | Me | H | —N(Me)—C(O)—NH—Me | —N(Me)—C(O)—NH—Me | HCl |
| 20 | H,H | Me | H | —N(Me)—C(O)—$CH_2$—N(piperazine)—N—Me | —N(Me)—C(O)—$CH_2$—N(piperazine)—N—Me | 5HCl |
| 21 | H,H | Me | H | OAc | OAc | HCl |
| 22 | H,H | Me | H | $OCO^tBu$ | $OCO^tBu$ | HCl |
| 23 | H,H | Me | H | $OCO(CH_2)_{14}Me$ | $OCO(CH_2)_{14}Me$ | HCl |
| 24 | H,H | Me | H | —O—C(O)—$NH_2$ | —O—C(O)—$NH_2$ | HCl |

TABLE 1-continued

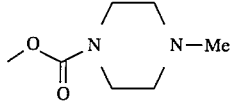

| Compd. | W¹,W² | R¹ | R² | R³ | R⁴ | Salt |
|---|---|---|---|---|---|---|
| 25 | H,H | Me | H |  | 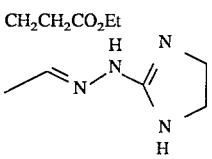 | 3HCl |
| 26 | H,H | Me | H | $CH_2CH_2CO_2Et$ | H | AcOH |
| 27 | H,H | Me | H | 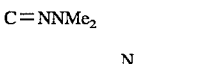 | H | 3HCl |
| 28 | H,H | Me | H | $C=NNMe_2$ | H | |
| 29 | H,H | Me | H | 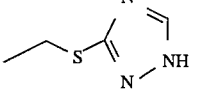 | H | 2HCl |
| 30 | H,H | Me | H | $CH_2S(CH_2)_2NMe_2$ | H | |
| 31 | H,H | Me | H | $CH_2O(CH_2)_2NMe_2$ | H | |
| 32 | H,H | Me | H | $CH_2SEt$ | $CH_2SEt$ | |
| 33 | H,H | Me | H | $CH_2S(CH_2)_2NMe_2$ | $CH_2OH$ | |
| 34 | O | Me | H | $CH_2OH$ | $CH_2OH$ | |
| 35 | H,H | Me | H | $OCO(CH_2)_7Me$ | $OCO(CH_2)_7Me$ | HCl |
| 36 | H,H | Me | H | $OCOCH_2(OCH_2CH_2)_3OMe$ | $OCOCH_2(OCH_2CH_2)_3OMe$ | |
| 37 | H,H | Me | H | $NHCO(CH_2)_{14}Me$ | $NHCO(CH_2)_{14}Me$ | HCl |
| 38 | H,H | Me | H | $NHCO(CH_2)_7Me$ | $NHCO(CH_2)_7Me$ | HCl |
| 39 | H,H | Me | H | $O(CH_2)_{15}Me$ | $O(CH_2)_{15}Me$ | HCl |
| 40 | H,H | Me | H | $O(CH_2)_8Me$ | $O(CH_2)_8Me$ | HCl |

Compound (I) and pharmaceutically acceptable salts thereof can be used as such or in the form of various pharmaceutical compositions according to their pharmacological activity and the intended administration purpose. The pharmaceutical compositions according to the present invention can be prepared by uniformly mixing an effective amount of Compound (I) or a pharmaceutically acceptable salt thereof as an active ingredient with pharmaceutically acceptable carriers. The carriers may have a wide range form depending on the type of the preparation desired for the administration. The pharmaceutical compositions are preferably formulated into a unit dose form which is suited to oral or non-oral administration. The dose forms for non-oral administration include ointments and injections.

Tablets can be prepared using, in a conventional manner, excipients such as lactose, glucose, sucrose, mannitol, and methyl cellulose; disintegrating agents such as starch, sodium alginate, calcium carboxymethyl cellulose, and crystalline cellulose; lubricants such as magnesium stearate and talc; binders such as gelatin, polyvinyl alcohol, polyvinylpyrrolidone, hydroxypropyl cellulose, and methyl cellulose; surface active agents such as sucrose fatty acid esters and sorbitol fatty acid esters; and the like. Tablets each containing 50 to 200 mg of an active ingredient are appropriate.

Granules can be prepared using, in a conventional manner, excipients such as lactose and sucrose; disintegrating agents such as starch; binders such as gelatin; and the like. Powders are prepared using excipients such as lactose and mannitol, and the like in a conventional manner. Capsules are prepared using, in a conventional manner, gelatin, water, sucrose, gum arabic, sorbitol, glycerin, crystalline cellulose, magnesium stearate, talc, etc. Capsules each containing 50 to 200 mg of an active ingredient are appropriate. Syrups are prepared using saccharides such as sucrose, water, ethanol, etc. in a conventional manner.

For the preparation of ointments, ointment bases such as vaseline, liquid paraffin, lanolin, and macrogol, and emulsifying agents such as sodium lauryl lactate, benzalkonium chloride, sorbitan monofatty acid esters, sodium carboxymethyl cellulose, and gum arabic, and the like may be used in a conventional manner.

Injectable preparations can be prepared using, in a conventional manner, solvents such as water, physiological saline, vegetable oil (e.g., olive oil and peanut oil), ethyl oleate, and propylene glycol; solubilizing agents such as sodium benzoate, sodium salicylate, and urethane; isotonizing agents such as sodium chloride and glucose; preservatives such as phenol, cresol, p-hydroxybenzoic esters, and chlorobutanol; antioxidants such as ascorbic acid and sodium pyrosulfite; and the like.

Compound (I) and pharmaceutically acceptable salts thereof may be administered orally or non-orally as an ointment or an injection. The effective dose and the administration schedule vary depending on the administration route, the age, body weight and symptoms of the patient, and the like, but generally ranges 6.0 to 300 mg/kg/day in a single to 4 divided doses.

The toxicity and pharmacological activity of Compound (I) will be described by way of Test Examples.

TEST EXAMPLE 1

Megakaryocyte colony formation-stimulating activity

An eight-weeks-old BALB/c mouse was killed. Its femurs and cervical vertebrae were taken out, and both end sections thereof were cut off. Bone marrow cells were collected from the pieces cut off from the femurs and cervical vertebrae using a syringe containing IMDM (430-2200EA prepared by Gibco Co.), and then blown into a test tube. The test tube was allowed to stand for 5 minutes, and the supernatant was collected with a piper. To a reaction mixture comprising the bone marrow cells (50,000 cells), bovine serum albumin (2%: A4508 made by Sigma Co.), transferrin (600 μg/ml: 652202 made by Boehringer Mannheim Co.), IL-3 (100 U/ml), cholesterol (16 μg/ml: 036-0641 made by Wako Co.) and agar (0.6%: 0142-02 made by Difco Laboratories) were separately added the test compounds at various concentrations, and 1 ml each of the mixtures was put into a 35-mm dish (Lux Co.), followed by incubation under the conditions of 37° C. 5% $CO_2$ and a humidity of 95% or more for 7 days. Separately, IL-3 alone was added to the bone marrow cells to prepare a control. After the incubation was completed, the agar was dried over a filter paper (1001-055 made by Whatman Co.) and then fixed with 2.5% glutaraldehyde, followed by acetylcholinesterase staining (ACHE staining).

The ACHE staining was carried out by the method described below.

ACHE staining: To each sample was added a solution comprising 0.67 mg/ml acetylthiocholine iodide, 2.94 mg/ml sodium citrate, 7.5 mg/ml copper (II) sulfate and 1.65 mg/ml potassium ferricyanide, and the mixture was allowed to stand at room temperature in the dark for 4–6 hours.

A group of 4 or more megakaryocytes which were stained reddish brown was regarded as a colony, and the number of colonies per dish was calculated using a microscope. The results are shown in Table 2 as relative values to the control.

(The table shows the relative values calculated on the basis of the control defined as 100.)

TABLE 2

| Compd. | Concn.(nM) | Rel. Value |
| --- | --- | --- |
| Control | — | 100 |
| 1 | 1 | 129 |
| 8 | 10 | 157 |
| 12 | 10 | 126 |
| 16 | 1 | 125 |
| 28 | 1 | 134 |
| 30 | 1 | 116 |

TEST EXAMPLE 2

Platelet Production-Stimulating Activity in Mice

A test compound was intraperitoneally administered to four 7-week-old male BALB/c mice per group once a day for consecutive 5 days (day 1 to day 5). A control group (4 mice per group) received only the solvent (5% Tween water). The blood was collected from the fundus oculi vein of each animal on the 15th day from the start of administration (day 15), and the number of the platelets was counted with a microcell counter (Model CC-180A, manufactured by Toa Iryo Denshi Co.). The rate of increase of the number of platelets in the test group (average) over the control (average) was calculated according to the following formula to evaluate the effect of the test compound. The results obtained are shown in Table 3.

TABLE 3

Rate of Increase = A/B × 100
A: the number of platelets in test group
B: the number of platelets in control group

| Test Compd. | Dose (mg/kg) | Rate of increase (%) |
| --- | --- | --- |
| 8 | 25 | 134 |
| 22 | 50 | 168 |
| 28 | 12.5 | 156 |

TEST EXAMPLE 3

Acute Toxicity

A solution (0.2 ml) of a test compound in phosphate-buffered physiological saline was intraperitoneally administered to a 6-week-old male DDY mice (3 mice per group). The 50% lethal dose ($LD_{50}$) was calculated from the survival rate after 24 hours from the administration. As a result, all the Compounds 1 to 40 tested had an $LD_{50}$ of not less than 10 mg/kg.

Certain embodiments of the present invention are illustrated in the following representative examples. In the following description, brine, $Na_2SO_4$, $NaHCO_3$, $CH_2Cl_2$, $CHCl_3$, MeOH, AcOEt, Cbz, and TLC, respectively stand for a saturated aqueous solution of sodium chloride solution, sodium sulfate, sodium hydrogen carbonate, dichloromethane, chloroform, methanol, ethyl acetate, benzyloxycarbonyl, and thin layer chromatography. In the following description, the position of the substituent which is bonded in the staurosporine skeleton is defined as follows; $R^1$ is bonded to a nitrogen at the 2-position, $R^2$ is bonded to a nitrogen at the 11-position, $R^3$ is bonded to a carbon at the 17-position, $R^4$ is bonded to a carbon at the 5-position, and W is bonded to a carbon at the 3-position. The staurosporine derivative, as the starting material, was prepared from staurosporine by such known processes as those given in WO89/07105, WO88/07045 and the like, or by a process analogous to those processes.

Example 1

Compound 1

To 11 mg (0.02 mmol) of 2-formylstaurosporine dissolved in 0.2 ml of THF and 0.2 ml of MeOH was added 4 mg (0.06 mmol) of sodium borohydride, followed by stirring at a room temperature for 1.5 hours. The reaction mixture was diluted with $CHCl_3$, then washed with water and brine, and then dried over $Na_2SO_4$. The solvent was removed by evaporation, and the residue was purified by preparative TLC ($MeOH/CHCl_3$ 5/95) to give 5 mg (51%) of Compound 1.

$^1HNMR(DMSO-d_6)$ δ;2.335(s,3H), 4.109(br.s,1H), 5.120(s,2H), 5.971(t,1H,J=6.9 Hz), 6.737 (br.s, 1H), 7.262–8.019 (m,7H), 9.290(d,1H,J=8.1 Hz).

Fab-MS(m/z); 497$(M+1)^+$

Example 2

Compound 2

To 1.8 g (3 mmol) of 11-Cbz-staurosporine dissolved in 30 ml of DMF was added 180 mg (4.5 mmol) of 60% sodium hydride at 0° C. followed by stirring for 10 minutes Then, 0.39 ml (4.5 mmol) of allyl bromide was added thereto at the same temperature, followed by stirring for 2.5 hours. The reaction mixture was diluted with $CHCl_3$, washed with water and brine, and then dried over $Na_2SO_4$. The solvent was removed by evaporation, and the residue was purified by silica gel column chromatography (AcOEt/toluene 1/9) to give 1.17 g (61%) of 2-allyl derivative.

$^1HNMR$ ($DMSO-d_6$, 90° C.) δ; 2.308(s,3H), 2.646(s,3H), 2.748(s,3H), 4.221(br.s,1H), 4.341(br.d,2H,J=5.6 Hz), 4.683(m,1H), 5.032(s,2H), 5.165–5.351(m,4H), 6.007–6.090(m,1H), 6.958(dd,1H,J=6.1,8.8 Hz), 7.259–7.512(m,9H), 8.039(d,1H,J=7.8 Hz), 9.310(d,1H,J= 8.1 Hz).

Fab-MS(m/z); 641$(M+1)^+$ 422 mg (0.66 mmol) of the 2-allyl derivative was dissolved in a mixture of 5 ml of $CHCl_3$ and 5 ml of acetone. A solution of 8.3 mg (0.033 mmol) of osmium tetroxide in 0.083 ml of acetone and 116 mg (0.99 mmol) of N-methylmorpholine oxide were added thereto, followed by stirring at room temperature for 1.5 hours. 10 ml of 8% sodium thiosulfate solution was added thereto and the mixture was stirred for 1 hour. Chloroform was added to the reaction mixture and the organic layer was separated, washed with brine and dried over $Na_2SO_4$. The solvent was removed by evaporation. The residue was purified by silica gel column chromatography ($MeOH/CHCl_3$ 5 /95) to give 422 mg (95%) of 11-Cbz derivative of Compound 2.

$^1HNMR(DMSO-d_6,90°$ C.) δ;2.312(s,3H), 2.636(s,3H), 2.746(s,3H), 3.489(d,2H,J=5.6 Hz), 3.686(m,1H), 3.850(m, 1H), 3.971(m,1H), 4.220(br.s,1H), 4.684(m,1H), 5.116–5.253(m,4H), 6.958(dd,1H,J=5.8,8.8 Hz), 7.256–7.513(m,9H), 7.583(d,1H,J=8.6 Hz), 8.032(d,1H,J= 7.3 Hz), 9.315(d,1H,J=7.8 Hz).

Fab-MS(m/z); 675$(M+1)^+$

To a solution of 30 mg (0.044 mmol) of the 11-Cbz derivative of Compound 2 dissolved in 1 ml of DMF was added 30 mg of 10% Pd/C, followed by stirring for 2 hours at 50° C. under a hydrogen atmosphere. The reaction mixture was filtered with celite and the solvent was removed by evaporation. The residue was purified by preparative TLC ($MeOH/CHCl_3$ 2/8), and then treated with 0.6N HCl/AcOEt to give 5.5 mg (21%) of hydrochloride of Compound 2.

$^1HNMR(DMSO-d_6,90°$ C.) δ; 2.191(m,1H), 2.417(s,3H), 2.675(s,3H), 3.504(d,2H,J=5.5 Hz), 3.686(m,1H), 3.664–3.731(m,1H), 3.825–3.883(m,1H), 3.975(m,2H), 4.520(s,1H), 5.126–5.223(m,2H), 6.903(dd,1H,J=3.6,9.3 Hz), 7.287–8.075(m,7H), 9.355(d,1H,J=7.9 Hz).

Fab-MS(m/z); 541$(M+1)^+$

Example 3

Compound 3

To a solution of 25 mg (0.037 mmol) of the 11-Cbz derivative of Compound 2 dissolved in 0.5 ml of THF was added under cooling with ice 18 mg (0.078 mmol) of sodium periodate dissolved in 0.3 ml of water, followed by stirring at room temperature for 3.5 hours. The reaction mixture was diluted with $CHCl_3$, washed with 5% aqueous sodium thiosulfate and brine, and then dried over $Na_2SO_4$. The solvent was removed by evaporation, and the residue was purified by preparative TLC ($MeOH/CHCl_3$ 5 /95) to give 19 mg (yield: 80%) of 2-(2-oxoethyl) derivative.

$^1HNMR(DMSO-d_6,90°$ C.) δ; 2.321(s,3H), 2.641(s,3H), 2.753(s,3H), 4.222(t,1H,J=1.8 Hz), 4.584(s,2H), 4.694(m, 1H), 5.141(s,2H), 5.184(d,1H,J=12.5 Hz), 5.238(d,2H,J= 12.4 Hz), 6.958(dd,1H,J=5.9,8.8 Hz), 7.259–8.026(m,12H), 9.257(d,1H,J=7.8Hz), 9.792(s,1H).

Fab-MS(m/z); 643$(M+1)^+$

11-Cbz derivative of Compound 3 was obtained from 64 mg (0.1 mmol) of the 2-(2-oxoethyl) derivative by the procedure analogous to that of Example 1 (yield:49 mg, 77%).

$^1HNMR(DMSO-d_6,$ 90° C.) δ;2.658(br.s,3H), 2.740(s, 3H), 4.270(br.s,1H), 4.691(m,1H), 4.895(t,1H,J=4.5 Hz), 5.160(s,2H), 5.198(s,2H), 7.010(br.s,1H), 7.276–8.073(m, 12H), 9.311(d,1H,J=7.8 Hz).

Fab-MS(m/z); 645$(M+1)^+$

Compound 3 was obtained from 25 mg (0.038 mmol) of the 11-Cbz derivative of Compound 3 by the procedure analogous to that of Example 2 (yield: 17 mg, 83%).

$^1HNMR(DMSO-d_6)$ δ;1.159(s,3H), 2.322(s,3H), 3.300(s, 3H), 3.737–3.827(m,4H), 4.061(d,1H,J=3.4 Hz), 4.614(t, 1H,J=4.9 Hz), 5.092(s,2H), 6.686(dd,1H,J=2.2,5.9 Hz), 7.227–7.984(m,7H), 9.313(d,1H,J=7.6 Hz).

Fab-MS(m/z); 511$(M+1)^+$

Example 4

Compound 4 and Compound 5

To a solution of 128 mg (0.2 mmol) of the 2-allyl-11-Cbz-staurosporine in 2 ml of THF was added 0.2 ml (0.2 mmol) of 1M borane-THF complex, followd by stirring at room temperature for 1 hour. To the reaction mixture were added 0.06 ml of water, 0.08 μl of 3M aqueous NaOH and 0.08 ml of 30% aqueous hydrogen peroxide, and the mixture was stirred at room temperature for 1 hour. The reaction mixture was diluted with $CHCl_3$, washed with water and brine, and then dried over $Na_2SO_4$. After the solvent was removed by evaporation, the residue was purified by preparative TLC (AcOEt/toluene 7/3) to give 40 mg (31%) of 11-Cbz derivative of Compound 4 and 37 mg (28%) of 11-Cbz derivative of Compound 5.

11-Cbz derivative of Compound 4

$^1HNMR(DMSO-d_6)$ δ; 1.936(quint, 2H,J=6.6 Hz), 2.670(br.s,3H), 2.738(s,3H), 3.555(t,2H,J=6.2 Hz), 3.715–3.830(m,2H), 4.271(br.s,1H), 5.099(s,2H), 5.195(s, 2H), 7.000(br.s,1H), 7.271–8.079(m,11H), 8.809(d,1H,J= 7.5 Hz), 9.304(dd,1H,J=1.0,8.0 Hz).

Fab-MS(m/z); 659(M+1)⁺

11-Cbz derivative of Compound 5

¹HNMR(DMSO-d₆) δ;1.178(d,3H,J=6.1 Hz), 2.664(br.s, 3H), 2.738(s,3H), 3.579–3.713(m,2H), 4.124(m,1H), 4.268(br.s,1H), 4.692(br.s,1H), 4.918(br.s,1H), 5.122–5.231(m,4H), 7.002(br.s,1H), 7.271–8.053(m,12H), 9.312(d,1H,J=7.8 Hz).

Fab-MS(m/z); 659(M+1)⁺

Compound 4 and Compound 5 were obtained from 28 mg (0.042 mmol) of the 11-Cbz derivative of Compound 4 and 25 mg (0.038 mmol) of the 11-Cbz derivative of Compound 5, respectively by the procedure analogous to that of Example 2 (yield of Compound 4: 13 mg, 59%; yield of Compound 5: 15 mg, 75%).

Compound 4

¹HNMR(DMSO-d₆) δ; 1.477(br.s,3H), 1.931(quint,2H,J= 6.5 Hz), 2.314(s,3H), 3.555(q,2H,J=6.1 Hz), 4.045(d,1H), 4.569(t,1H,J=5.2 Hz), 5.053(s,2H), 6.718(t,1H,J=3.5 Hz), 7.246–7.998(m,7H), 9.287(d,1H,J=7.4 Hz).

Fab-MS(m/z); 525(M+1)⁺

Compound 5

¹HNMR(DMSO-d₆) δ;1.180(d,3H,J=6.1 Hz), 1.476(br.s, 3H), 2.314(s,3H), 4.083(d,1H,J=3.5 Hz), 4.108(m,1H), 4.912(dd,1H,J=4.0,4.6 Hz), 5.084–5.177(m,2H), 6.718(t, 1H,J=3.7 Hz), 7.244–8.000(m,7H), 9.294(dd,1H,J=0.9,7.9 Hz).

Fab-MS(m/z); 525(M+1)⁺

Example 5

Compound 6 and Compound 7

To a solution of 480 mg (1 mmol) of 2-methyl staurosporine in 20 ml of dichloroethane was added 0.28 ml (3 mmol) of dichloromethyl methyl ether and 0.32 ml (3 mmol) of titanium tetrachloride, followed by stirring at room temperature for 2 hours. The reaction mixture was diluted with CHCl₃ and poured to a saturated aqueous solution of NaHCO₃, and the resulting organic layer was separated, washed with brine, and then dried over Na₂SO₄. The solvent was removed by evaporation and the residue was purified by silica gel column chromatography (MeOH/CHCl₃ 2/98) to give 378 mg of a mixture of 17-formyl derivative and 5,17-diformyl derivative.

Compound 6 and Compound 7 were obtained from 51 mg (0.1 mmol) of the resulting mixture by the procedure analogous to that of Example 1 (yield of Compound 6: 44 mg, 86% yield of Compound 7: 7 mg, 13%).

Compound 6

¹HNMR(DMSO-d₆) δ;1.440(br.s,3H), 2.310(s,3H), 4.073(d,1H,J=3.4 Hz), 4.676(d,2H,J=5.7 Hz), 5.025(s,2H), 5.116(t,1H,J=5.8 Hz), 6.995(t,1H,J=3.6 Hz), 7.265–7.992(m,7H), 9.232(d,1H,J=1.0 Hz).

Fab-MS(m/z); 511(M+1)⁺

Compound 7

¹HNMR(DMSO-d₆) δ;4.081(br.s,1H), 4.683(t,4H,J=6.0 Hz), 5.020(s,2H), 5.118(t,1H,J=5.6 Hz), 5.116(t,1H,J=5.7 Hz), 6.704(br.s,1H), 7.371–7.940(m,5H), 9.228(d,1H,J=1.0 Hz).

Fab-MS(m/z); 541(M+1)⁺

Example 6

Compound 8

To a solution of 102 mg (0.2 mmol) of Compound 6 in 2 ml of acetic acid were added 0.077 ml (1 mmol) of trifluoroacetic acid and 0.096 ml (0.6 mmol) of triethylsilane, followed by stirring at room temperature for 5.5 hours. The reaction mixture was diluted with CHCl₃, poured to a saturated aqueous solution of NaHCO₃, and then the organic layer was separated and washed with brine, and dried over potassium carbonate (K₂CO₃). After the solvent was removed by evaporation, the residue was purified by preparative TLC (MeOH/CHCl₃ 5/95) to give 50 mg (51%) of Compound 8.

¹HNMR(DMSO-d₆) δ;1.494(br.s,3H), 2.310(s,3H), 2.520(s,3H), 3.257(s,3H), 4.081(br.s,1H), 5.018(s,2H), 6.675(br.t,1H,J=3.6 Hz), 7.270–7.988(m,6H), 9.105(t,1H,J= 0.7 Hz).

Fab-MS(m/z); 495(M+1)⁺

Example 7

Compound 9

To a solution of 99 mg (0.185 mmol) of Compound 7 in 1 ml of dichloromethane were added 0.18 ml(1.1 mmol) of triethylsilane and 1.0 ml (13 mmol) of trifluoroacetic acid in an argon atmosphere, followd by stirring overnight at room temperature. To the reaction mixture were added ice and an aqueous sodium hydroxide to stop the reaction, followed by extraction with dichloromethane. The extract was washed with brine and dried over MgSO₄, and the solvent was removed by evaporation. The residue was purified by TLC (CHCl₃/MeOH/triethylamine 25/1/1) and dissolved in a mixed solvent of 1 ml of chloroform and 2 ml of AcOEt. 0.10 ml of 0.88N HCl (dissolved in AcOEt) was added to the solution and the mixture was stirred at room temperature for 1 hour. The resulting precipitate was collected by filtration, and washed with AcOEt and dried under reduced pressure to give 12 mg (19%) of Compound 9.

¹HNMR(DMSO-d₆) δ;2.0–2.2(m, 1H), 2.267(s,3H), 2.465 (s,3H), 2.527(s,3H), 2.548(s,3H), 2.688(br.s,3H), 3.271(s,3H), 3.9–4.1(br.s,1H), 4.398(br.s,1H), 5.072(s,2H), 6.87–6.90 (m,1H), 7.32–7.37(m,2H), 7.453(d,1H,J=8.1 Hz), 7.877(s,1H), 7.949(d,1H,J=8.8 Hz), 8.5–8.7(br.s,2H), 9.139(d,1H,J=0.7 Hz).

Fab-MS(m/z); 509(M+1)⁺

Example 8

Compound 10

A solution of 5.43 g (40.7 mmol) of aluminum chloride in 200 ml of CH₂Cl₂ was cooled to 0° C., and 5.76 ml (81.4 mmol) of acetyl chloride was added thereto, followed by stirring for 30 minutes. The mixture was cooled to −78° C. A solution of 5.00 g (8.14 mmol) of 2-methyl-11-Cbz-staurosporine in 50 ml of CH₂Cl₂ was added dropwise to the mixture, followed by stirring for 1 hour. The reaction was stopped by the addition of a saturated aqueous solution of sodium hydrogen carbonate, followed by extraction with CHCl₃. The extract was washed with water and brine, and then dried over Na₂SO₄. The solvent was removed by evaporation and the residue was purified by silica gel column chromatography (MeOH/CHCl₃ 1/200) to give 4.73 g (83% of 5,17-diacetyl derivative.

¹HNMR(DMSO-d₆) δ; 2.690(s,6H), 2.738(s,3H), 2.755(s,3H), 5.234(s,4H), 7.077(br.s,1H), 7.402(br.s,5H), 7.724(d,1H,J=8.6 Hz), 8.086–8.106(m,3H), 8.587(s,1H), 10.032(s,1H)

Fab-MS(m/z); 565(M+1)⁺

A solution of 159 mg (0.23 mmol) of the 5,17-diacetyl derivative in 10 ml of CH₂Cl₂ and 5 ml of MeOH was cooled to 0° C., and 26 mg (0.68 mmol) of sodium borohydride was added thereto, followed by stirring for 3.5 hours. After the completion of reaction, the mixture was diluted with CHCl₃, washed with brine, and then dried over $Na_2SO_4$. After the solvent was removed by evaporation, the residue was purified by silica gel column chromatography ($MeOH/CHCl_3$ 1/20) to give 140 mg (87%) of 5,17-bis(2-hydroxyethyl) derivative.

$^1HNMR(DMSO-d_6, 90°$ C.) δ; 1.429–1.479(m,6H), 2.288(s,3H), 2.636(s,3H), 2.744(s,3H), 3.289(s,3H), 4.191(s,1H), 4.688(d,1H,J=11.0 Hz), 4.917–4.997(m,2H), 5.041(s,2H), 5.193(d,1H,J=12.5 Hz), 5.251(d,1H,J=12.5 Hz), 6.923(dd,1H,J=5.9,8.0 Hz), 7.516–7.348(m,8H), 7.833(dd,1H,J=3.4,8.8 Hz), 7.999(dd,1H,J=1.7,12.2 Hz), 9.297(d,1H,J=9.0 Hz)

Fab-MS(m/z);702(M)$^+$

To a solution of 140 mg (0.20 mmol) of the 5,17-bis(2-hydroxyethyl) derivative in 5 ml of $CH_2Cl_2$ was added 191 μl (1.20 mmol) of triethylsilane and 1.53 ml (19.9 mmol) of trifluoroacetic acid, followed by stirring at room temperature for 10 minutes. The mixture was made basic with 1.0N NaOH, followed by extraction with $CHCl_3$, and the extract was washed with brine and dried over $Na_2SO_4$. The solvent was removed by evaporation and the residue was purified by preparative TLC ($MeOH/CHCl_3$ 3/100) to give 107 mg (80%) of 11-Cbz derivative of Compound 10. $^1HNMR(DMSO-d_6$, 90° C.) δ; 1.302–1.364(m,6H), 2.275(s,3H), 2.625(s,3H), 2.740(s,3H), 2.793–2.876(m,4H), 3.278(s,3H), 4.173(s,1H), 4.640–4.690(m,1H), 5.039(s,2H), 5.190(d,1H, J=12.5 Hz), 5.248(d,1H,J=12.5 Hz), 6.909(dd,1H,J=5.8,8.8 Hz), 7.301–7.478(m,8H), 7.794(d,1H,J=8.6 Hz), 7.827(s, 1H), 9.175(s,1H)

Fab-MS(m/z); 671(M+1)$^+$

To a solution of 106 mg (0.16 mmol) of the 11-Cbz derivative of Compound 10 in 10 ml of DMF was added 100 mg of 10% Pd/C, followed by stirring under a hydrogen atmosphere at room temperature for 3.5 hours. After the completion of reaction, the reaction mixture was filtered with celite and the solvent was removed by evaporation. The residue was dissolved in 5 ml of $CHCl_3$ and ml of 0.88N HCl/AcOEt was added thereto, followed by stirring for 1 hour. The resulting precipitate was filtered off to give 72 mg (79%) of Compound 10. $^1HNMR(DMSO-d_6, 90°$ C.) δ; 1.306–1.408(m,6H), 2.137–2.206(m,1H), 2.444(s,3H), 2.583(br.s,3H), 2.802–2.885(m,4H), 3.281(s,3H), 3.885(br.s,1H), 4.462(s,1H), 5.046(s,2H), 6.847(dd,1H,J= 3.2,9.0 Hz), 7.325–7.356(m,2H), 7.435(d,1H,J=7.8 Hz), 7.852(s,1H), 7.915(d,1H,J=8.8 Hz), 9,202(s,1H)

Fab-MS(m/z);537(M+1)$^+$

Example 9

Compound 11

To a solution of 5 mg (0.01 mmol) of 2-methyl-17-formylstaurosporine in 0.2 ml of dichloroethane was added 7 mg of (carboethoxymethylene)triphenylphosphorane and the mixture was stirred at room temperature overnight, followed by stirring at 50° C. for 6 hours. The reaction mixture was washed with brine and dried over $K_2CO_3$. The solvent was removed by evaporation and the residue was purified by preparative TLC ($MeOH/CHCl_3$ 1/9) to give 5 mg (86%) of Compound 11.

$^1HNMR(DMSO-d_6)$ δ; 1.312(t,3H,J=7.1 Hz), 1.420(br.s, 3H), 2.315(s,3H), 3.394(s,3H), 4.080(d,1H,J=3.5 Hz), 4.229(q,2H,J=7.1 Hz), 5.058(s,2H), 6,571(d,1H,J=15.8 Hz), 6.751(m,1H), 7.281–8.002(m,7H), 9.581(d,1H,J=1.5 Hz).

Fab-MS(m/z); 579(M+1)$^+$

Example 10

Compound 12

To 20 ml of $CH_2Cl_2$ cooled to 0° C., 108 μl (1.22 ml) of trifluoromethanesulfonic acid and 52 μl (1.22 mmol) of fuming nitric acid were added, followed by stirring for 20 minutes. To the reaction mixture cooled to −78° C. was added dropwise, a solution of 500 mg (0.81 mmol) of 11-Cbz-staurosporine in 5 ml of $CH_2Cl_2$, followed by stirring for 1 hour. The reaction was stopped by the addition of a saturated aqueous solution of sodium hydrogen carbonate. The reaction mixture was extracted with $CHCl_3$ and the extract was washed with water and brine, and then dried over $Na_2SO_4$. After the solvent was removed by evaporation, the residue was purified by silica gel column chromatography ($MeOH/CHCl_3$ 1/100) to give 537 mg (99%) of 17-nitro derivative.

$^1HNMR(DMSO-d_6)$ δ; 2.125–2.232(m,1H), 2.322(s,3H), 2.635(s,3H), 2.708(s,3H), 3.300(s,3H), 3.394(br.s,1H), 4.602(br.s,1H), 5.020(s,2H), 5.186(s,2H), 7.104(br.s,1H), 7.362–7.450(m,6H), 7.543(t,1H,J=7.9 Hz), 7.834(d,1H,J= 9.1 Hz), 8.123(d,1H,J=8.0 Hz), 8.362(dd,1H,J=2.2,9.0 Hz), 8.724(s,1H), 10.231(d,1H,J=2.4 Hz)

Fab-MS(m/z);660(M+1)$^+$

Compound 12 was obtained from 200 mg (0.30 mmol) of the 17-nitro derivative and 100 mg of 10% Pd/C by the procedure analogous to that of Example 8 (yield: 145 mg, 84%).

$^1HNMR(DMSO-d_6)$ δ; 2.066–2.183(m,1H), 2.283(s,3H), 2.675(s,3H), 3.284(s,3H), 4.043(br.s,1H), 4.562(s,1H), 5.112(s,2H), 6.990(dd,1H,J=2.8,9.5 Hz), 7.429(t,1H,J=7.5 Hz), 7.517–7.587(m,2H), 7.704(d,1H,J=10.7 Hz), 8.088–8.174(m,2H), 9.163(br.s,1H), 9.407(d,1H,J=2.1 Hz), 10.204(br.s,1H)

Fab-MS(m/z);496(M+1)$^+$

Example 11

Compound 13

A solution of 518 mg (0.80 mmol) of 2-methyl-11-Cbz-17-nitrostaurosporine in 25 ml of THF was cooled to 0° C. and 74 mg (1.1 mmol) of zinc powder and 2.5 ml of 2N HCl were added thereto, followed by stirring for 30 minutes. The mixture was further stirred at room temperature for 1 day. After the completion of reaction, the reaction mixture was filtered. A saturated aqueous solution of sodium hydrogen carbonate was added to the filtrate, followed by extraction with $CHCl_3$. The extract was washed with water and brine, and then dried over $Na_2SO_4$. After the solvent was removed by evaporation, the residue was purified by silica gel column chromatography ($MeOH/CHCl_3$ 1/50) to give 271 mg (54%) of 11-Cbz derivative of Compound 12.

$^1HNMR(DMSO-d_6)$ δ; 2.333(br.s,3H), 2.671(br.s,6H), 2.737(s,3H), 3.257(s,3H), 4.254(br.s,1H), 4.653(br.s,1H), 5.029(s,2H), 5.187(s,2H), 6.849(br.s,1H), 6.893(dd,1H,J= 2.2,8.6 Hz), 7.324–7.482(m,8H), 8.019(d,1H,J=7.7 Hz), 8.554(s,1H)

Fab-MS(m/z);630(M+1)$^+$

To a solution of 200 mg (0.32 mmol) of the 11-Cbz derivative of Compound 12 in 10 ml of THF and 1 ml of water, was added 200 mg (3.2 mmol) of sodium cyanoborohydride and 890 μl (31.8 mmol) of formaldehyde. The mixture was adjusted to pH 5–6 with 2N hydrochloric acid, and stirred at room temperature for 1.5 hours. After the completion of reaction, the reaction mixture was diluted with $CHCl_3$ and washed successively with a saturated aqueous solution of $NaHCO_3$, water and brine, and then dried over Na$_2$SO$_4$. The solvent was removed by evaporation and the residue was purified by silica gel column chromatography (MeOH/CHCl$_3$ 1/50) to give 88 mg (42%) of 11-Cbz derivative of Compound 13.

$^1$HNMR(CDCl$_3$) δ; 1.750(br.s,3H), 2.184(br.s,1H), 2.469(s,3H), 2.496(s,3H), 2.802(s,3H), 3.137(s,3H), 3.389(s,3H), 4.036(br.s,1H), 4.651(br.s,1H), 4.947(s,2H), 5.190(s,2H), 6.678(br.s,1H), 7.184–7.516(m,8H), 7.735(br, d,1H,J=6.9 Hz), 7.927(s,1H), 7.945(s,1H), 9.221(br.s,1H)

Fab-MS(m/z);658(M+1)$^+$

Compound 13 was obtained from 102 mg (0.16 mmol) of the 11-Cbz derivative of Compound 13 and 50 mg of 10% Pd/C by the procedure analogous to that of Example 8 (yield: 73 mg, 78%).

$^1$HNMR(DMSO-d$_6$) δ; 2.258(s,3H), 2.667(s,6H), 2.735(s,3H), 2.893(s,3H), 3.284(s,3H), 4.038(br.s,1H), 4.565(s,1H), 5.106(d,1H,J=18.0 Hz), 5.151(d,1H,J=18.2 Hz), 6.983(dd,1H,J=3.2,9.4 Hz), 7.447(t,1H,J=7.4 Hz), 7.588(t,1H,J=7.4 Hz), 7.768(br.s,1H), 7.887(br.s,1H), 7.953(s,1H), 8.094(d,1H,J=3.1 Hz), 8.106(s,1H), 9.201(br.s, 1H), 9.522(br.s,1H)

Fab-MS(m/z);524(M+1)$^+$

Example 12

Compound 14

A solution of 87 mg (0.41 mmol) of N-Cbz-glycine in 10 ml of CH$_2$Cl$_2$ was cooled to 0° C. and 87 mg (0.41 mmol) of 3-(3-diethylaminopropyl)-1-ethylcarbodiimide.hydrochloride and 200 mg (0.32 mmol) of the 11-Cbz derivative of Compound 12 were added thereto, followd by stirring under an argon atmosphere at room temperature for 1 hour. The reaction was stopped by an addition of ice water, and the reaction mixture was extracted with CHCl$_3$. The extract was washed with a saturated aqueous solution of NaHCO$_3$ and brine, and then dried over Na$_2$SO$_4$. The solvent was removed by evaporation,and the residue was purified by silica gel column chromatography (MeOH/CHCl$_3$ 3/100) to give 213 mg (82%) of 17-(N-Cbz-glycyl)amino derivative.

$^1$HNMR(DMSO-d$_6$, 90° C.) δ; 2.302(s,3H), 2.625(s,3H), 2.749(s,3H), 3.276(s,3H), 3.927(d,2H,J=6.1 Hz), 4.649–4.699(m,1H), 5.031(s,2H), 5.101(s,2H), 5.194(d,1H, J=12.4 Hz), 5.253(d,1H,J=12.5 Hz), 6.927(dd,1H,J=5.9,8.8 Hz), 7.094(br.s,1H), 7.262–7.517(m,13H), 7.827(d,1H,J= 8.8 Hz), 7.893(d,1H,J=8.3 Hz), 8.041(d,1H,J=7.8 Hz), 9.303(d,1H,J=2.2 Hz), 9.748(s,1H)

Fab-MS(m/z);821(M+1)$^+$

Compound 14 was obtained from 213 mg (0.26 mmol) of the 17-(N-Cbz-glycyl)amino derivative and 106 mg of 10% Pd/C by the procedure analogous to that of Example 8 (yield: 113 mg, 70%).

$^1$HNMR(DMSO-d$_6$) δ;2.067–2.136(m,1H), 2.319(s,3H), 2.672(s,3H), 3.273(s,3H), 3.847(d,2H,J=5.6 Hz), 4.038(br.s, 1H), 4.581(s,1H), 5.091(s,2H), 6.942(dd,1H,J=3.2,9.5 Hz), 7.433(t,1H,J=7.6 Hz), 7.535–7.571(m,2H), 7.896(dd,1H,J= 2.2,8.8 Hz), 8.070–8.097(m,2H), 8.235(br.s,2H), 9.436(d, 1H,J=1.9 Hz), 9.199(br.s,1H), 9.523(br.s,1H), 10.622(s,1H)

Fab-MS(m/z);553(M+1)$^+$

Example 13

Compound 15

A solution of 250 mg (0.40 mmol) of the 11-Cbz derivative of Compound 12 in 10 ml of CH$_2$Cl$_2$ was cooled to 0° C. and 55 μl (0.40 mmol) of triethylamine and 35 μl (0.44 mmol) of chloroacetyl chloride were added thereto, followed by stirring for 30 minutes. After the completion of reaction, the reaction mixture was diluted with CHCl$_3$, washed with water and brine, and then dried over Na$_2$SO$_4$. The solvent was removed by evaporation, and the residue was purified by silica gel column chromatography (MeOH/CHCl$_3$ 1/100) to give 190 mg (69%) of 17-chloroacetyl-amino derivative.

$^1$HNMR(DMSO-d$_6$) δ; 2.201–2.281(m,1H), 2.332(br.s, 3H), 2.670(s,3H), 2.743(s,3H), 3.276(s,3H), 4.274(br.s,1H), 4.309(s,1H), 4.672(br.s,1H), 5.077(s,2H), 5.195(s,2H), 6.972(br.s,1H), 7.312–7.387(m,7H), 7,503(t,1H,J=7.8 Hz), 7.596(d,1H,J=8.8 Hz), 7.894(dd,1H,J=2.2,8.8 Hz), 8.298(d, 1H,J=7.3 Hz), 9.303(d,1H,J=2.2Hz), 10.418(s,1H)

Fab-MS(m/z);706(M+1)$^+$

To a solution of 150 mg (0.21 mmol) of the 17-chloroacetyl-amino derivative in 10 ml of CHCl$_3$ were added successively 148 μl (1.1 mmol) of triethylamine, 185.2 μl (1.1 mmol) of diisopropylethylamine and 118 μl (1.1 mmol) of N-methylpiperazine, followed by stirring at 60° C. for 9 hours. After the completion of reaction, the reaction mixture was diluted with CHCl$_3$, washed with water and brine, and then dried over Na$_2$SO$_4$. The solvent was removed by evaporation, and the residue was purified by silica gel column chromatography (MeOH/CHCl$_3$ 7.5/100) to give 128 mg (78%) of 11-Cbz derivative of Compound 15.

$^1$HNMR(DMSO-d$_6$) δ; 2.215(s,3H), 2.738(s,3H), 3.171(s,2H), 3.273(s,3H), 4.279(br.s,1H), 4.681(br.s,1H), 5.074(s,2H), 5.194(s,2H), 6.970(br.s,1H), 7.352–7.399(m, 6H), 7.486–7.515(m,1H), 7. 569(d,1H,J=8.5 Hz), 7.832(dd, 1H,J=2.1,8.8 Hz), 8.054(d,1H,J=7.7 Hz), 9.268(d,1H,J=2.0 Hz), 9.720(s,1H)

Fab-MS(m/z);770(M+1)$^+$

Compound 15 was obtained from 128 mg (1.17 mmol) of the 11-Cbz derivative of Compound 15 and 64 mg of 10% Pd/C by the procedure analogous to that of Example 8 (yield: 103 mg, 83%).

$^1$HNMR(DMSO-d$_6$) δ; 2.070–2.131(m,1H), 2.313(s,3H), 2.672(s,3H), 2.856(s,3H), 3.275(s,3H), 4.020–4.032(m,1H), 4.586(s,1H), 5.093(s,2H), 6.942(dd,1H,J=3.3,9.4 Hz), 7.414(t,1H,J=7.6 Hz), 7.553(s,1H), 7.555(s,1H), 7.870(dd, 1H,J=2.2,8.7 Hz), 8.080(d,1H,J=3.9 Hz), 8.098(d,1H,J=2.4 Hz), 9.220(br.s,1H), 9.431(s,1H), 9.549(br.s,1H), 10.451(br.s,1H), 10.247(br.s,1H)

Fab-MS(m/z);636(M+1)$^+$

Example 14

Compound 16

5,17-Dinitro derivative was obtained from 500 mg (0.81 mmol) of 2-methyl-11-Cbz-staurosporine, 540 μl (6.11 mmol) of trifluoromethanesulfonic acid and 258 μl (6.11 mmol) of fuming nitric acid by the procedure analogous to that of Example 10 (yield: 200 mg, 35%).

$^1$HNMR(DMSO-d$_6$) δ; 2.115–2.200(m,1H), 2.361(s,3H), 2.617(s,3H), 2.711(s,3H), 3.255(s,3H), 3.372(br.s,1H), 4.635(br.s,1H), 5.188(s,4H), 7.087(t,1H,J=7.1 Hz), 7.409(br.s,5H), 7.776(d,1H,J=9.0 Hz), 8.189(br.s,1H), 8.287(dd,1H,J=2.4,9.1 Hz), 8.366(d,1H,J=8.8 Hz), 8.781(d, 1H,J=2.4 Hz), 10.148(d,1H,J=2.4 Hz)

Fab-MS(m/z);705(M+1)$^+$

Compound 16 was obtained from 175 mg (0.25 mmol) of the 5,17-dinitro derivative and 88 mg of 10% Pd/C by the procedure analogous to that of Example 8 (yield: 135 mg, 94%).

$^1$HNMR(DMSO-d$_6$) δ; 2.054–2.149(m,1H), 2.295(s,3H), 2.671(s,3H), 4.036(s,1H), 4.556(s,1H), 5.061(s,2H), 6.986(dd,1H,J=3.2,9.0 Hz), 7.455(d,1H,J=7.1 Hz), 7.542(dd,1H,J=2.2,8.7 Hz), 7.708(d,1H,J=8.7 Hz), 7.969(s, 1H), 8.153(d,1H,J=9.1 Hz), 9.395(d,1H,J=2.0 Hz).

Fab-MS(m/z);511(M+1)$^+$

Example 15

Compound 17

11-Cbz derivative of Compound 16 was obtained from 1.0 g of 2-methyl-11-Cbz-5,17-dinitrostaurosporine, 0.93 g of zinc powder and 10 ml of 2N HCl by the procedure analogous to that of Example 11 (yield: 573 mg, 63%).

$^1$HNMR(DMSO-$d_6$) δ;2.216–2.205(m,1H), 2.263(s,3H), 2.624(s,3H), 2.727(s,3H), 3.246(s,3H), 4.126(br.s,1H), 4.929(s,2H), 5.001(br.s,2H), 5.146(br.s,2H), 5.176(s,2H), 6.800–6.822(m,1H), 6.843(d,1H,J=2.2 Hz), 6.864(d,1H,J= 2.2 Hz), 7.181(d,1H,J=2.1 Hz), 7.286(d,1H,J=8.8 Hz), 7.396(br.s,5H), 7.679–7.699(m,1H), 8.530(d,1H,J=2.0 Hz)

Fab-MS(m/z);645(M+1)$^+$

11-Cbz derivative of Compound 17 was obtained from 200 mg (0.31 mmol) of the 11-Cbz derivative of Compound 16, 195 mg (3.10 mmol) of sodium cyanoborohydride and 861 µl (31.0 mmol) of formaldehyde by the procedure analogous to that of Example 11 (yield: 97 mg, 45%).

$^1$HNMR(DMSO-$d_6$) δ; 2.626(s,3H), 2.727(s,3H), 3.045(s,6H), 3.068(s,3H), 3.277(s,3H), 4.206(br.s,1H), 4.658(br.s,1H), 5.079(s,2H), 5.185(s,2H), 6.922(br.s,1H), 7.135(br.s,1H), 7.332(br.s,5H), 7.547(br.s,2H), 7.665–7.722(m,1H), 7.841(br.s,1H), 8.076(s,1H)

Fab-MS(m/z);701(M+1)$^+$

Compound 17 was obtained from 97 mg (0.14 mmol) of the 11-Cbz derivative of Compound 17 and 100 mg of 10% Pd/C by the procedure analogous to that of Example 8 (yield: 60 mg, 68%).

$^1$HNMR(DMSO-$d_6$,90° C.) δ; 2.113–2.167(m,1H), 2.383(s,3H), 2.658(s,3H), 3.164(s,3H), 3.220(s,3H), 3.304(s,2H), 3.904(br.s,1H), 4.578(s,1H), 5.105(s,2H), 6.922–6.937(m,1H), 7.517(br.s,1H), 7.681(br.d,1H,J=9.0 Hz), 7.747(br.s,1H), 7.855(br.s,1H), 8.031(d,1H,J=9.3 Hz), 9.135(br.s,2H), 9.494(s,1H), 9.641(br.s,1H)

Fab-MS(m/z);567(M+1)$^+$

Example 16

Compound 18

5,17-Bis(N-Cbz-glycylamino) derivative was obtained from 200 mg (0.31 mmol) of the 11-Cbz derivative of Compound 16, 149 mg (0.71 mmol) of N-Cbz-glycine and 86 mg (0.71 mmol) of 3-(3-diethylaminopropyl)-1-ethylcarbodiimide.hydrochloride by the procedure analogous to that of Example 12 (yield: 198 mg, 62%).

$^1$HNMR(DMSO-$d_6$,90° C.) δ; 2.267–2.280(m,1H), 2.293(s,3H), 2.633(s,3H), 2.744(s,3H), 3.284(s,3H), 3.908(d,2H,J=2.7 Hz), 3.924(d,2H,J=2.7 Hz), 4.181(s,1H), 4.641–4.680(m,1H), 4.985(s,2H), 5.097(s,2H), 5.101(s,2H), 5.195(d,1H,J=12.5 Hz), 5.246(d,1H,J=12.5 Hz), 6.931(dd, 1H,J=5.8,8.7 Hz), 7.169(br.s,2H), 7.268–7.450(m,15H), 7.521(d,1H,J=8.8 Hz), 7.661(dd,1H,J=2.2,9.0 Hz), 7.817(dd,1H,J=2.0,8.8 Hz), 7.851(d,1H,J=9.3 Hz), 8.349(d, 1H,J=2.0 Hz), 9.289(d,1H,J=2.0 Hz), 9.748(s,1H), 9.824(s,1H)

Fab-MS(m/z);1027(M+1)$^+$

Compound 18 was obtained from 198 mg (0.19 mmol) of the 5,17-bis(N-Cbz-glycylamino) derivative and 100 mg of 10% Pd/C by the procedure analogous to that of Example 8 (yield: 81 mg, 57%).

$^1$HNMR(DMSO-$d_6$, 90° C.) δ; 2.114–2.307(m,1H), 2.422(s,3H), 2.644(s,3H), 3.279(s,3H), 3.821(s,2H), 3.856(s,2H), 3.921(br.s,1H), 4.591(s,1H), 4.994(s,2H), 6.903(dd,1H,J=3.4,9.3 Hz), 7.532(d,1H,J=8.6 Hz), 7.727(dd,1H,J=2.2,9.0 Hz), 7.831(d,1H,J=8.3 Hz), 8.013(d, 1H,J=9.0 Hz), 8.206(br.s,3H), 8.444(d,1H,J=2.0 Hz), 9.426(d,1H,J=1.7 Hz), 10.422(s,1H), 10.756(s,1H)

Fab-MS(m/z); 625(M+1)$^+$

Example 17

Compound 19

To a solution of 200 mg (0.31 mmol) of the 11-Cbz derivative of Compound 16 in 10 ml of $CH_2Cl_2$ was added 91.6 µl (1.6 mmol) of methyl isocyanate and the mixture was heated under reflux for 2 hours. After the completion of reaction, the reaction mixture was diluted with $CHCl_3$, washed with water and brine, and then dried over $Na_2SO_4$. The solvent was removed by evaporation, and the residue was purified by silica gel column chromatography (MeOH/$CHCl_3$ 1/20) to give 147 mg (63%) of 11-Cbz derivative of Compound 19.

$^1$HNMR(DMSO-$d_6$,90° C.) δ; 2.266(s,3H), 2.622(s,3H), 2.699(s,3H), 2.723(s,3H), 2.741(s,3H), 3.274(s,3H), 4.144(s,1H), 4.640–4.668(m,1H), 4.693(s,2H), 5.188(d,1H, J=12.5 Hz), 5.243(d,1H;J=12.7 Hz), 5.783(br.s,1H), 5.862(br.s,1H), 6.882(dd,1H,J=5.8,8.8 Hz), 7.325–7.442(m, 7H), 7.751(d,1H,J=9.8 Hz), 7.778(dd,1H,J=2.2,8.8 Hz), 8.138(d,1H,J=2.2 Hz), 8.230(br.s,1H), 8.321(br.s,1H), 9.029(d,1H,J=2.2 Hz)

Fab-MS(m/z); 759(M+1)$^+$

Compound 19 was obtained from 147 mg (0.19 mmol) of the 11-Cbz derivative of Compound 19 and 150 mg of 10% Pd/C by the procedure analogous to that of Example 8 (yield: 104 mg, 81%).

$^1$HNMR(DMSO-$d_6$, 90° C.) δ; 2.086–2.157(m,1H), 2.393(s,3H), 2.437(s,3H), 2.666(s,3H), 2.702(s,3H), 2.724(s,3H), 3.274(s,3H), 3.936(br.s,1H), 4.452(s,1H), 4.971(s,2H), 6.842(dd,1H,J=3.4,9.3 Hz), 7.397(d,1H,J=8.8 Hz), 7.482(dd,1H,J=2.2,9.0 Hz), 7.837(dd,1H,J=2.2,9.0 Hz), 7.866(d,1H,J=9.0 Hz), 8.191(d,1H,J=2.2 Hz), 8.332(br.s,1H), 8.494(br.s,1H), 8.818(br.s,1H), 9.051(d,1H, J=2.0 Hz), 9.198(br.s,1H)

Fab-MS(m/z);625(M+1)$^+$

Example 18

Compound 20

5,17-Bis(chloroacetylamino) derivative was obtained from 200 mg (0.31 mmol) of the 11-Cbz derivative of Compound 16, 87 µl (0.62 mmol) of triethylamine and 57 µl (0.71 mmol) of chloroacetyl chloride by the procedure analogous to that of Example 13 (yield: 129 mg, 52%).

$^1$HNMR(DMSO-$d_6$) δ; 2.193–2.365(m,1H), 2.661(s,3H), 2.738(s,3H), 4.231(br.s,1H), 4.308(s,2H), 4.323(s,2H), 4.671(br.s,1H), 5.031(s,2H) 5.195(s,2H), 6.974(br.s,1H), 7.399(br.s,5H), 7.586(d,1H,J=8.5 Hz), 7.684 (d,1H,J=9.1 Hz), 7 893(dd,1H,J=2.0,8.8 Hz), 8.383(d,1H,J=2.0 Hz), 9.296(d,1H,J=2.0 Hz), 10.413(s,1H), 10.437(s,1H)

Fab-MS(m/z);797(M)$^+$

11-Cbz derivative of Compound 20 was obtained from 129 mg (0.16 mmol) of the 5,17-bis(chloroacetylamino) derivative, 226 µl (1.6 mmol) of triethylamine, 283 µl (1.6 mmol) of diisopropylethylamine and 180 µl (1.6 mmol) of N-methylpiperazine by the procedure analogous to that of Example 13 (yield: 138 mg, 92%).

$^1$HNMR(DMSO-$d_6$,90° C.) δ; 2.222(s,6H), 2.287(s,3H), 2.434–2.456(m,4H), 2.554–2.613(m,4H), 2.744(s,3H), 3.163(s,2H), 3.180(s,2H), 3.289(s,3H), 4.184(s,1H), 4.682(br.d,J=11.5 Hz), 5.000(s,2H), 5.193(d,1H,J=12.5 Hz), 5.246(d,1H,J=12.5 Hz), 6.933(dd,1H,J=5.8,8.6 Hz), 7.345–7.449(m,5H), 7.525(d,1H,J=8.8 Hz), 7.680(dd,1H,J=

2.0,9,0 Hz), 7.783–7.839(m,2H), 8.362(d,1H,J=1.7 Hz), 9.264(d,1H,J=1.7 Hz), 9.466(s,1H), 9.584(s,1H)

Fab-MS(m/z);925(M+1)$^+$

Compound 20 was obtained from 128 mg (0.14 mmol) of the 11-Cbz derivative of Compound 20, and 130 mg of 10% Pd/C by the procedure analogous to that of Example 8 (yield: 113 mg, 84%).

$^1$HNMR(DMSO-d$_6$,90° C.) δ; 2.417(s,3H), 2.467(s,3H), 2.663(s,3H), 2.777(s,6H), 3.289(s,3H), 3.511(s,2H), 3.552(s,2H), 3.942(br.s,1H), 4.578(s,1H), 5.009(s,2H), 6.898(dd,1H,J=3.7,9.3 Hz), 7.504(d,1H,J=8.8 Hz), 7.747(dd,1H,J=2.2,9,0 Hz), 7.827(dd,1H,J=2.0,8.8 Hz), 7.977(d,1H,J=9.0 Hz), 8.442(d,1H,J=2.2 Hz), 9.071(br.s, 1H), 9.360(d,1H,J=2.0 Hz), 9.633(br.s,1H), 9.902(s,1H)

Fab-MS(m/z);791(M+1)$^+$

Example 19

Compound 21

To a solution of 4.5 g (6.44 mmol) of 2-methyl-11-Cbz-5,17-diacetyl staurosporine in 450 ml of CH$_2$Cl$_2$ was added 2.17 g (25.8 mmol) of sodium hydrogen carbonate and 8.34 g (48.4 mmol) of 55% m-chloroperbenzoic acid, followed by stirring at room temperature for 5 hours. After the completion of reaction, the reaction mixture was diluted with CHCl$_3$, washed succesively with a saturated aqueous solution of sodium sulfite, a saturated aqueous solution of sodium hydrogen carbonate and water, and then dried over Na$_2$SO$_4$. The solvent was removed by evaporation and the residue was dissolved in 250 ml of CH$_2$Cl$_2$ and cooled to 0° C. 3.15 ml (12.9 mmol) of 28% sodium methoxide in MeOH was added thereto followed by stirring for 10 minutes. After the completion of reaction, the reaction mixture was neutralized with 2N HCl, followed by extraction with CHCl$_3$. The extract was washed with brine, and then dried over Na$_2$SO$_4$. The solvent was removed by evaporation, and the residue was purified by silica gel column chromatography (MeOH/CHCl$_3$ 1/20) to give 2.67 g (63%) of 5,17-dihydroxy derivative.

$^1$HNMR(DMSO-d$_6$) δ; 2.635(s,3H), 2.733(s,3H), 4.137(br.s,1H), 4.635(br.s,1H), 4.977(s,2H), 5.181(s,2H), 6.855(br.s,1H), 6.937–6.973(m,2H), 7.300–7.571(m,6H), 7.646–7.718(m,2H), 8.716(s,1H), 9.007(s,1H), 9.208(s,1H)

Fab-MS(m/z);646(M)$^+$

11-Cbz derivative of Compound 21 was obtained from 50 mg (0.077 mmol) of the 5,17-dihydroxy derivative, 54 μl (0.39 mmol) of triethylamine and 27.5 μl (0.39 mmol) of acetyl chloride by the procedure analogous to that of Example 13 (yield: 52 mg, 92%).

$^1$NMR(DMSO-d$_6$) δ; 2.213–2.327(m,1H), 2.353(s,6H), 2.690(s,3H), 2.745(s,3H), 3.244(s,3H), 4.298(br.s,1H), 4.663(br.s,1H), 5.047(s,2H), 5.198(s,2H), 7.006(br.s,1H), 7.251(d,1H,J=2.4 Hz), 7.273(d,1H,J=2.4 Hz), 7.400(br.s, 5H), 7.623(d,1H,J=8.8 Hz), 7.801(d,1H,J=2.5 Hz), 7.994(br.s,1H), 8.994(d,1H,J=2.4 Hz)

Fab-MS(m/z);731(M+1)$^+$

Compound 21 was obtained from 150 mg (0.21 mmol) of the 11-Cbz derivative of Compound 21 and 75 mg of 10% Pd/C by the procedure analogous to that of Example 8 (yield: 120 mg, 92%).

$^1$HNMR(DMSO-d$_6$) δ; 2.045–2.134(m,1H), 2.273(s,3H), 2.363(s,6H), 2.669(s,3H), 3.239(s,3H), 4.022(br.s,1H), 4.510(s,1H), 5.003(s,2H), 6.925(dd,1H,J=3.1,9.4 Hz), 7.274–7.386(m,2H), 7.580(d,1H,J=8.8 Hz), 7.803(d,1H,J= 2.4 Hz), 8.106(d,1H,J=9.0 Hz), 9.024(d,1H,J=2.5 Hz)

Fab-MS(m/z);597(M+1)$^+$

Example 20

Compound 22

11-Cbz derivative of Compound 22 was obtained from 150 mg (0.23 mmol) of 2-methyl-11-Cbz-5,17-dihydroxy staurosporine, 162 μl (1.2 mmol) of triethylamine and 143 μl (1.2 mmol) of pivaloyl chloride by the procedure analogous to that of Example 19 (yield: 113 mg, 60%).

$^1$HNMR(DMSO-d$_6$, 90° C.) δ; 1.391(s,9H), 1.402(s,9H), 2.302(s,3H), 2.673(s,3H), 2.755(s,3H), 3.259(s,3H), 4,231(s,1H), 4.650–4.700(m,1H), 5.033(s,2H), 5.197(d,1H, J=12.5 Hz), 5.248(d,1H,J=12.2 Hz), 6.981(dd,1H,J=6.0,8.7 Hz), 7.168–7.224(m,2H), 7.325–7 450(m,7H), 7.615(d,1H, J=8.5 Hz), 7.719(d,1H,J=2.2 Hz), 7.929(d,1H,J=9.3 Hz), 9.005(d,1H,J=2.4 Hz)

Fab-MS(m/z);815(M+1)$^+$

Compound 22 was obtained from 110 mg (0.13 mmol) of the 11-Cbz derivative of Compound 22 and 50 mg of 10% Pd/C by the procedure analogous to that of Example 8 (yield: 85 mg, 88%).

$^1$HNMR(DMSO-d$_6$, 90° C.) δ; 1.396–1.404(m,18H), 2.187–2.246(m,1H), 3.260(s,3H), 3.888(br.s,1H), 4.468(s, 1H), 5.035(s,2H), 6.904(dd,1H,J=3.3,8.9 Hz), 7.193–7.252(m,2H), 7.571(d,1H,J=8.6 Hz), 7.736(d,1H,J= 2.4 Hz), 8.045(d,1H,J=9.0 Hz), 9.030(d,1H,J=2.4 Hz)

Fab-MS(m/z);681(M+1)$^+$

Example 21

Compound 23

11-Cbz derivative of Compound 23 was obtained from 150 mg (0.23 mmol) of 2-methyl-11-Cbz-5,17-dihydroxystaurosporine, 162 μl (1.2 mmol) of triethylamine and 319 μ(1.2 mmol) of palmitoyl chloride by the procedure analogous to that of Example 19 (yield: 235 mg, 90%).

$^1$HNMR(DMSO-d$_6$, 90° C.) δ;0.874(t,6H,J=6.8,6.8 Hz), 1.259–1.481(m,48H), 1.717–1.780(m,4H), 2.316(s,3H), 2.618–2.655(m,4H), 2.667(s,3H), 2.766(s,3H), 3.261(s,3H), 4.233(s,1H), 4.675–4.702(m,1H), 5.013(s,2H), 5.210(d,1H, J=12.5 Hz), 5.261(s,1H,J=12.5 Hz), 6.973(dd,1H,J=5.9,8.5 Hz), 7.229(dd,1H,J=2.4,8.8 Hz), 7.260(dd,1H,J=2.4,9.2 Hz), 7.356–7.463(m,5H), 7.607(d,1H,J=8.5 Hz), 7.751(d, 1H,J=2.2 Hz), 7.931(d,1H,J=9.3 Hz), 9.041(d,1H,J=2.6 Hz)

Fab-MS(m/z); 1123(M+1)$^+$

Compound 23 was obtained from 235 mg (0.21 mmol) of the 11-Cbz derivative of Compound 23 and 120 mg of 10% Pd/C by the procedure analogous to that of Example 8 (yield: 193 mg, 90%).

$^1$HNMR(DMSO-d$_6$, 90° C.) δ;0.846(t,1H,J=6.5 Hz), 1,248–1.703(m,48H), 1.703–1.784(m,4H), 2.156–2.225(m, 1H), 2.612–2.657(m,4H), 3.251(s,3H), 3.948(br.s,1H), 4.474(s,1H), 5.014(s,2H), 6.915(dd,1H,J=3.4,9.0 Hz), 7.251(dd,1H,J=2.2,8.8 Hz), 7.287(dd,1H,J=2.4,9.3 Hz), 7.562(d,1H,J=8.3 Hz), 7.771(d,1H,J=2.4 Hz), 8.045(d,1H, J=9.0 Hz), 9.048(d,1H,J=2.0 Hz)

Fab=MS (m/z);989(M+1)$^+$

Example 22

Compound 24

A solution of 150 mg (0.23 mmol) of 2-methyl-11-Cbz-5,17-dihydroxystaurosporine in 10 ml of THF was cooled to 0° C. and 101 μl (1.2 mmol) of chlorosulfonyl isocyanate was added thereto, followed by stirring for 1.5 hours. To the reaction mixture were added 10 ml of THF and 3 ml of water and stirred at 70° C. for 1 hour. After the completion of reaction, the reaction mixture was diluted with CHCl$_3$ and washed with brine, and then dried over Na$_2$SO$_4$. The solvent was removed by evaporation, and the residue was purified by silica gel column chromatography (MeOH/CHCl$_3$ 3/20) to give 110 mg (65%) of 11-Cbz derivative of Compound 24.

$^1$HNMR(DMSO-d$_6$) δ; 2.344(br.s,3H), 2.689(s,3H), 2.744(s,3H), 3.251(s,3H), 4.272(br.s,1H), 4.680(br.s,1H), 5.061(s,2H), 5.195(s,2H), 6.992(br.s,1H), 7.220(d,1H,J=2.4 Hz), 7.237(d,1H,J=2.4 Hz), 7.398(br.s,5H), 7.598(d,1H,J= 8.8 Hz), 7.710(d,1H,J=2.4 Hz), 7.960(d,1H,J=8.8 Hz), 8.971(d,1H,J=2.4 Hz)

Fab-MS(m/z);733(M+1)$^+$

Compound 24 was obtained from 110 mg (0.15 mmol) of the 11-Cbz derivative of Compound 24 and 100 mg of 10% Pd/C by the procedure analogous to that of Example 8 (yield: 76 mg, 80%).

$^1$HNMR(DMOS-d$_6$) δ;2.075–2.143(m,1H), 2.294(s,3H), 2.671(s,3H), 3.249(s,3H), 4.022(br.s,1H), 4.501(s,1H), 5.051(s,2H), 6.931(dd,1H,J=2.9,9.3 Hz), 7.240–7.293(m, 2H), 7.540(d,1H,J=8.5 Hz), 7.742(d,1H,J=2.5 Hz), 8.052(d, 1H,J=9.0 Hz), 9.000(d,1H,J=2.4 Hz), 9.232(br.s,1H)

Fab-MS(m/z);599(M+1)$^+$

Example 23

Compound 25

A solution of 300 mg (0.46 mmol) of 2-methyl-11-Cbz-5,17-dihydroxystaurosporine in 15 ml of THF was cooled to 0° C. and 324 μl (2.3 mmol) of triethyl amine and 468 mg (2.3 mmol) of 4-nitrophenyl chloroformate were added thereto, followed by stirring for 8 hours. After the completion of reaction, the reaction mixture was diluted with CHCl$_3$ and washed with a saturated aqueous solution of sodium hydrogen carbonate and brine then dried over Na$_2$SO$_4$. The solvent was removed by evaporation, and the residue was purified by preparative TLC (MeOH/CHCl$_3$ 1/100) to give 6 mg (26%) of 5,17-bis(4-nitrophenyloxycarbonyl) derivative.

$^1$HNMR(DMSO-d$_6$) δ; 2.720(s,3H), 2.751(s,3H), 3.275(s,3H), 4.311(br.s,1H), 4.672(br.s,1H), 5.100(s,2H), 5.204(s,2H), 7.055(t,1H,J=7.2Hz), 7.410(br.s,5H), 7.582(d, 1H,J=2.5 Hz), 7.604(d,1H,J=2.4 Hz), 7.733(s,1H), 7.749–7.795(m,4H), 8.122(d,1H,J=2.7 Hz), 8.362–8.420(m, 4H), 9.236(d,1H,J=2.5 Hz)

Fab-MS(m/z);977(M+1)$^+$

To a solution of 150 mg (0.15 mmol) of the 5,17-bis(4-nitrophenyloxycarbonyl) derivative in 10 ml of CHCl$_3$ were added 107 μl (0.77 mmol) of triethylamine and 85 μl (0.77 mmol) of N-methylpiperazine and the mixture was stirred at room temperature for 4 hours. After the completion of reaction, the reaction mixture was diluted with CHCl$_3$ and washed successively with a saturated aqueous solution of sodium hydrogen carbonate, water and brine, and dried over Na$_2$SO$_4$. The solvent was removed by evaporation, and the residue was purified by silica gel column chromatography (MeOH/CHCl$_3$ 1/10) to give 121 mg (88%) of 11-Cbz derivative of Compound 25.

$^1$HNMR(DMSO-d$_6$) δ; 2.265(s,9H), 2.427(br.s,8H), 2.675(s,3H), 2.742(s,4H), 3.245(s,3H), 3.487(br.s,4H), 3.683(br.s,4H), 4.264(br.s,1H), 4.672(br.s,1H), 5.050(s,2H), 5.194(s,2H), 6.985(br.s,1H), 7.232(d,1H,J=2.5 Hz), 7.254(d, 1H,J=2.4 Hz), 7.402(br.s,5H), 7.610(d,1H,J=8.8 Hz), 7.748(d,1H,J=2.4 Hz), 7.957(br.s,1H), 8.976(br.s,1H)

Fab-MS(m/z);899(M+1)$^+$

Compound 25 was obtained from 121 mg (0.13 mol) of the 11-Cbz derivative of Compound 25 and 60 mg of 10% Pd/C by the procedure analogous to that of Example 8 (yield: 94 mg, 80%).

$^1$HNMR(DMSO-d$_6$) δ; 2.411(s,3H),2.664(s,3H),2.833(s, 3H), 2.837(s,3H), 3.259(s,3H), 3.467(br.s,4H), 3.954(br.s, 1H), 4.234(br.s,4H), 4.608(s,1H), 5.038(s,2H), 6.937(dd, 1H,J=3.4,9.3 Hz), 7.315(dd,1H,J=2.5,8.8 Hz), 7.367(dd,1H, J=2.4,9.0 Hz), 7.571(d,1H,J=8.8 Hz), 7.838(d,1H,J=2.4 Hz), 8.056(d,1H,J=9.3 Hz), 9.055(br.s,1H), 9.090(d,1H,J=2.2 Hz), 9.626(br.s,1H), 11.342(br.s,1H)

Fab-MS(m/z);765(M+1)$^+$

Example 24

Compound 26

To a solution of 5 mg (0.009 mmol) of Compound 11 in 0.2 ml of DMF were added 3 mg of 20% Pd(OH)$_2$/C and 0.1 ml of acetic acid and the mixture was stirred under hydrogen atmosphere at room temperature for 1 hour. The reaction mixture was filtered with celite, and the solvent was removed by evaporation. The residue was purified by preparative TLC (MeOH/CHCl$_3$ 1/9) to give 3 mg (yield: 58%) of Compound 26.

$^1$HNMR(DMSO-d$_6$) δ; 1.173(t,3H,J=7.1 Hz), 1.454(s, 3H), 2.300(s,3H), 3.064(t,2H,J=7.7 Hz), 3.332(s,3H), 4.077(q,2H,J=7.1 Hz), 5.020(s,1H), 6.668(t,1H,J=3.6 Hz), 7.264–7.994(m,6H), 9.144(d,1H,J=1.3 Hz)

Fab-MS(m/z); 581(M+1)$^+$

Example 25

Compound 27

To a solution of 60 mg (0.118 mmol) of 2-methyl-17-formylstaurosporine in a mixture of 3 ml of THF and 2 ml of MeOH, was added 0.5 ml of an aqueous solution of 107 mg (0.59 mmol) of 2-hydrazino-2-imidazolin hydrobromide, and the mixture was adjusted to pH 2–4 with 3N hydrochloric acid, and stirred at room temperature for 2 hours. The reaction mixture was diluted with CHCl$_3$ and washed succesively with a saturated aqueous solution of NaHCO$_3$, water and brine, and then dried over K$_2$CO$_3$. The solvent was removed by evaporation and the residue was purified by preparative TLC (28% NH$_4$OH/MeOH/CHCl$_3$ 0.5/5/95) and treated with 0.8N HCl/AcOEt to give 28 mg (36%) of Compound 27.

$^1$HNMR(DMSO-d$_6$) δ; 2.093(m,1H), 2.294(s,3H), 2.671(br.s,3H), 3.759(s,3H), 4.035(m,1H), 4.593(br.s,1H), 5.105(s,2H), 7.006(dd,1H,J=3.3,9.4 Hz), 7.403–8.243(m, 6H), 8.459(s,1H), 9.447(d,1H,J=1.7 Hz), 12.551(s,1H).

Fab-MS(m/z); 591(M+1)$^+$

Example 26

Compound 28

Compound 28 was obtained from 60 mg (0.118 mol) of 2-methyl-17-formylstaurosporine and 57 mg (0.59 mmol) of dimethylhydrazine hydrochloride by the procedure analogous to that of Example 25 (yield:30 mg, 46%).

$^1$HNMR(DMSO-d$_6$) δ;1.453(br.s,3H), 2.309(s,3H), 2.928(s,6H), 4.072(d,1H,J=3.4 Hz), 5.034(s,2H), 6.703(br.s, 1H), 7.269–7.994(m,7H), 9.351(d,1H,J=1.7 Hz).

Fab-MS(m/z); 551(M+1)$^+$

Example 27

Compound 29

To a solution of 60 mg (0.117 mmol) of Compound 6 and 120 mg (1.17 mmol) of 1H-1,2,4-triazole-3-thiol in 3 ml of CHCl$_3$ was added 543 mg (2.34 mmol) of camphorsulfonic acid, followed by stirring at room temperature for 3.5 hours. The reaction mixture was diluted with CHCl$_3$ and washed with a saturated aqueous solution of NaHCO$_3$ and brine, and then dried over K$_2$CO$_3$. The solvent was removed by evaporation and the residue was purified by silica gel column chromatography (28% NH₄OH/MeOH/CHCl₃ 0.5/5/95) and treated with 0.8N HCl/AcOEt to give 41 mg (53%) of Compound 29.

¹HNMR(DMSO-d₆) δ;1.458(br.s,3H), 2.294(s,3H), 4.093(br.s,1H), 4.581(s,2H), 5.037(s,2H), 6.704(br.s,1H), 7.279–8.020(m,6H), 8.429(br.s,1H), 9.307(s,1H), 14. 051(br.s,1H).

Fab-MS(m/z); 594(M+1)⁺

Example 28

Compound 30

Compound 30 was obtained from 60 mg (0.117 mol) of Compound 6 and 165 mg (1.17 mmol) of 2-dimethylaminoethanethiol hydrochloride by the procedure analogous to that of Example 27 (yield:51 mg, 73%).

¹HNMR(DMSO-d₆) δ;1.446(s,3H), 2.105(s,6H), 2.305(s, 3H), 3.955(s,2H), 4.068(d,1H,J=3.4 Hz), 5.027(s,2H), 6.691(t,1H,J=3.5 Hz), 7.261–7.993(m,6H), 9.231(d,1H,J= 1.3 Hz).

Fab-MS(m/z); 598(M+1)⁺

Example 29

Compound 31

Compound 31 was obtained from 60 mg (0.117 mol) of Compound 6 and 0.12 ml (1.17 mmol) of 2-dimethylaminoethanol by the procedure analogous to that of Example 27 (yield: 16 mg, 23%).

¹HNMR(DMSO-d₆) δ;1.439(s,3H), 2.213(s,6H), 2.309(s, 3H), 3.597(t,2H,J=6.0 Hz), 4.072(d,1H,J=3.7 Hz), 4.646(s, 2H), 5.031(s,2H), 6.705(t,1H,J=3.5 Hz), 7.268–7.995(m, 6H), 9.252(d,1H,J=1.3 Hz).

Fab-MS(m/z); 582(M+1)⁺

Example 30

Compound 32

Compound 32 was obtained from 54 mg (0.1 mmol) of Compound 7 and 0.15 ml (2 mmol) of ethanethiol by the procedure analogous to that of Example 27 (yield: 46 mg, 73%).

¹HNMR(DMSO-d₆) δ;1.222(t,3H,J=7.3 Hz), 1.245(t,3H, J=7.3 Hz), 2.294(s,3H), 3.271(s,3H), 3.946(s,2H), 3.759(s, 2H), 4.061(d,1H,J=3.4 Hz), 5.015(s,2H), 6.686(t,1H,J=3.4 Hz), 7.368–7.931(m,5H), 9.222(d,1H,J=1.2 Hz).

Fab-MS(m/z); 629(M+1)⁺

Example 31

Compound 33

Compound 33 was obtained from 54 mg (0.1 mmol) of Compound 7 and 283 mg (2 mmol.) of 2-dimethylaminoethanethiol hydrochloride by the procedure analogous to that of Example 27 (yield: 17 mg, 27% ).

¹HNMR(DMSO-d₆) δ;1.457(s,3H), 2.116(s,6H), 2.300(s, 3H), 3.954(s,2H), 4.057(d,1H,J=3.4 Hz), 4.688(s,2H), 5.018(s,2H), 5.158(t,1H,J=5.7 Hz), 6.689(t,1H,J=3.5 Hz), 7.366–7.935(m,5H), 9.226(d,1H,J=1.3 Hz).

Fab-MS(m/z); 628(M+1)⁺

Example 32

Compound 34

To a solution of 432 mg (0.87 mmol) of 2-methyl-3-oxostaurosporine in 20 ml of dichloroethane was added 0.63 ml (7 mmol) of dichloromethyl methyl ether and 0.6 ml (4.4 mmol) of titanium tetrachloride and the mixture was stirred at room temperature for 1.5 hours. The reaction mixture was diluted with CHCl₃ and poured to a saturated aqueous solution of NaHCO₃ and the organic layer was separated, washed with brine, and then dried over Na₂SO₄. The solvent was removed by evaporation to give 1.93 g of 5,17-diformyl derivative as a crude product.

Compound 34 was obtained from 15 mg of the resulting 5,17-diformyl derivative by a procedure analogous to that of Example 1 (yield: 7 mg, 46%).

¹HNMR(DMSO-d₆) δ;1.416(br.s,3H), 2.324(s,3H), 4.079(d,1H,J=3.4 Hz), 4.682(d,2H,J=5.6 Hz), 4.721(d,2H, J=5.8 Hz), 5.152(t,1H,J=5.7 Hz), 5.222(t,1H,J=5.8 Hz), 6.718(br.s,1H), 7.452–7.969(m,4H), 9.061(s,1H), 9.173(s, 1H).

Fab-MS(m/z); 555(M+1)⁺

Example 33

Compound 35

11-Cbz derivative of Compound 35 was obtained from 150 mg (0.23 mmol) of 2-methyl-11-Cbz-5,17-dihydroxystaurosporine, 162 μl (1.16 mmol) of triethylamine and 209 μl (1.16 mmol) of pelargonoyl chloride by the procedure analogous to that of Example 13 (yield: 193 mg, 90%).

¹HNMR(DMSO-d₆,90°C.) δ; 0.841–0.901(m,6H), 1.256–1.519(m,20H), 1.692–1.773(m,4H), 2.322(s,3H), 2.610–2.658(m,4H), 2.670(s,3H), 2.749(s,3H), 3.245(s,3H), 4.239(s,1H), 4.649–4.678(m,1H), 5.023(s,2H), 5.181(d,1H, J=12.2 Hz), 5.229(d,1H,J=12.5 Hz), 6.974(dd,1H, J=6.0,8.7 Hz), 7.201–7.253(m,2H), 7.331–7.456(m,5H), 7.613(d,1H, J=8.8 Hz), 7.746(d,1H,J=2.4 Hz), 7.934(d,1H,J=9.0 Hz), 9.006(d,1H,J=2.4 Hz).

Fab-MS(m/z);927(M+1)⁺

Compound 35 was obtained from 170 mg (0.18 mmol) of the 11-Cbz derivative of Compound 35 and 100 mg of 10% Pd/C by the procedure analogous to that of Example 8 (yield: 138 mg, 91%). ¹HNMR(DMSO-d₆) δ; 0.843–0.899(m,6H), 1.244–1.483(m,20H), 1.684–1.749(m, 4H), 2.071–2.120(m,1H), 2.276(s,3H), 2.648–2.678(m,4H), 3.237(s,3H), 4.024(br.s,1H), 4.510(s,1H), 5.020(dd,2H,J= 18.1,25.7 Hz), 6.916(dd,1H,J=3.0,9.3 Hz), 7.261(dd,1H,J= 2.4,9.0 Hz), 7.293(dd,1H,J=2.4,9.1 Hz), 7.573(d,1H,J=8.8 Hz), 7.770(d, 1H,J=2.4 Hz), 8.093(d,1H,J=9.1 Hz), 8.993(br.s,1H), 9.011(d,1H,J=2.4 Hz), 9.237(br.s,1H).

Fab-MS(m/z);793(M+1)⁺

Example 34

Compound 36

11-Cbz derivative of Compound 36 was obtained from 150 mg (0.23 mmol) of 2-methyl-11-Cbz-5,17-dihydroxystaurosporine, 432 μl (3.10 mmol) of triethylamine and 176 mg (3.10 mmol) of 3,6,9,10-tetraoxatridecanoyl chloride by the procedure analogous to that of Example 13 (yield: 162 mg, 66%).

¹HNMR(DMSO-d₆,90°C.) δ; 2.319(s,3H), 2.669(s,3H), 2.754(s,3H), 3.253(s,3H), 3.390(s,6H), 3.563–3.837(m, 24H), 4.133(s,2H), 4.175(s,2H), 4.236(s,1H), 4.652–4.698(m,1H), 5.020(s,2H), 5.203(d,1H,J=12.4 Hz), 5.243(d,1H,J=12.5 Hz), 6.973(dd,1H,J=6.0,8.6 Hz), 7.209(dd,1H,J=2.4,8.9 Hz), 7.258(dd,1H,J=2.2,9.0 Hz), 7.344–7.456(m,5H), 7.610(d,1H,J=9.0 Hz), 7.749(d,1H,J= 2.2 Hz), 7.933(d,1H,J=9.0 Hz), 9.023(d,1H,J=2.2 Hz).

Fab-MS(m/z);1055(M+1)⁺

Compound 36 was obtained from 150 mg (0.14 mmol) of the 11-Cbz derivative of Compound 36 and 100 mg of 10% Pd/C by the procedure analogous Co that of Example 8 (yield: 52 mg, 40%).

¹HNMR(DMSO-d₆) δ; 1.603(br,s,1H), 2.248(s,3H), 3.233(s,3H), 3.254(s,3H), 3.420(s,6H), 3.801–3.542(m, 24H), 4.107(s,2H), 4.132(s,2H), 5.009(s,2H), 6.878(dd,1H, J=3.0,8.9 Hz), 7.161(dd,1H,J=2.4,9.1 Hz), 7.193(dd,1H,J= 2.3,9.0 Hz), 7.472(d,1H,J=2.4 Hz), 7.564(d,1H,J=8.9 Hz), 8.097(d,1H,J=9.0 Hz), 9.008(d,1H,J=2.2 Hz).

Fab-MS(m/z);921(M+1)⁺

Example 35

Compound 37

11-Cbz derivative of Compound 37 was obtained from 150 mg (0.23 mmol) of the 11-Cbz derivative of Compound 16, 81 μl (0.58 mmol) of triethylamine and 160 mg (0.58 mmol) of palmitoyl chloride by the procedure analogous to that of Example 13 (yield: 147 mg, 56%).

¹HNMR(DMSO-d₆, 90°C.) δ;0.823–0.874(m,6H), 1.124–1.411(m,48H), 1.621–1.695(m,4H), 2.281(s,3H), 2.329–2.382(m,4H), 2.627(s,3H), 2.740(s,3H), 3.282(s,3H), 4.167(s,1H), 4.635–4.686(m,1H), 4.974(s,2H), 5.175(d,1H, J=12.5 Hz), 5.227(d,1H,J=12.5 Hz), 6.895(dd,1H,J=5.9,8.5 Hz), 7.342–7.447(m,5H), 7.472(d,1H,J=8.8 Hz), 7.660(dd, 1H,J=2.0,9.0 Hz), 7.791–7.822(m,2H), 8.336(d,1H,J=2.0 Hz), 9.240(d,1H,J=2.0 Hz), 9.631(s,1H), 9.692(s,1H).

Fab-MS(m/z);1121(M+1)⁺

Compound 37 was obtained from 147 mg (0.13 mmol) of the 11-Cbz derivative of Compound 37 and 75 mg of 10% Pd/C by the procedure analogous to that of Example 8 (yield: 114 mg, 85%).

¹HNMR(DMSO-d₆) δ; 0.864–0.898(m,6H), 1.267–1.371(m,48H), 1.665–1.719(m,4H), 2.071–2.142(m, 1H), 2.328(s,3H), 2.379–2.432(m,4H), 2.509(s,3H), 2.731(s,3H), 4.072(br.s,1H), 4.451(s,1H), 5.053(s,2H), 6.935(dd,1H,J=3.1,9.4 Hz), 7.516(d,1H,J=8.8 Hz), 7.743(dd,1H,J=2.1,9.2 Hz), 7.976(dd,1H,J=2.0,8.8 Hz), 8.032(d,1H,J=9.3 Hz), 8.485(d,1H,J=2.0 Hz), 8.915(br.s, 2H), 9.311(d,1H,J=2.2 Hz), 10.018(s,1H), 10.085(s,1H).

Fab-MS(m/z);987(M+1)⁺

Example 36

Compound 38

11-Cbz derivative of Compound 38 was obtained from 133 mg (0.21 mmol) of the 11-Cbz derivative of Compound 16, 72 μl (0.51 mmol) of triethylamine and 93 μl (0.51 mmol) of pelargonoyl chloride by the procedure analogous to that of Example 13 (yield: 79 mg, 42%).

¹HNMR(DMSO-d₆, 90° C.) δ; 0.843–0.889(m,6H), 1.255–1.419(m,20H), 1.624–1.717(m,4H), 2.283(s,3H), 2.332–2.385(m,4H), 2.628(s,3H), 2.741(s,3H), 3.283(s,3H), 4.169(s,1H), 4.635–4.686(m,1H), 4.978(s,2H), 5.176(d,1H, J=12.5 Hz), 5.228(d,1H,J=12.5 Hz), 6.899(dd,1H,J=5.7,8.7 Hz), 7.326–7.449(m,6H), 7.477(d,1H,J=8.8 Hz), 7.661(dd, 1H,J=2.2,9.0 Hz), 7.807(d,1H,J=9.3 Hz), 8.336(d,1H,J=2.0 Hz), 9.242(d,1H,J=2.0 Hz), 9.635(s,1H), 9.697(s,1H).

Fab-MS(m/z);925(M+1)⁺

Compound 38 was obtained from 79 mg (0.086 mmol) of the 11-Cbz derivative of Compound 38 and 40 mg of 10% Pd/C by the procedure analogous to that of Example 8 (yield: 60 mg, 85%).

¹HNMR(DMSO-d₆) δ; 0.855–0.886(m,6H), 1.237–1.331(m,20H), 1.607–1.679(m,4H), 2.028–2.097(m, 1H), 2.296(s,3H), 2.339–2.393(m,4H), 2.466(s,3H), 2.674(s,3H), 4.008(br.s,1H), 4.456(s,2H), 5.014(s,2H), 6.895(dd,1H,J=2.9,9.3 Hz), 7.474(d,1H,J=9.0 Hz), 7.697(dd,1H,J=2.0,9.3 Hz), 7.926(dd,1H,J=2.0,8.8 Hz), 7.990(d,1H, J=9.0 Hz), 8.455(d,1H,J=2.0 Hz), 8.943(br.s, 1H), 9.179(br.s,1H), 9.274(d,1H,J=2.0 Hz), 9.979(s,1H), 10.064(s,1H).

Fab-MS(m/z);791(M+1)⁺

Example 37

Compound 39

A solution of 200 mg (0.31 mmol) of 2-methyl-11-Cbz-5,17-dihydroxystaurosporine in 6 ml of DMF was cooled to 0° C. and 37 mg (0.93 mmol) of 60% sodium hydride was added thereto, followed by stirring for 30 minutes. To the reaction mixture was added 473 μl (1.55 mmol) of 1-bromohexadecane, followed by stirring for 3 hours. After the reaction was stopped by an addition of a saturated ammonium chloride aqueous solution, the reaction mixture was extracted with AcOEt. The extract was washed with brine, and dried over Na₂SO₄. The solvent was removed by evaporation, and the residue was purified by silica gel column chromatography (MeOH/CHCl₃ 1/200) to give 228 mg (82%) of 11-Cbz derivative of Compound 39.

¹HNMR(CDCl₃) δ; 0.876(t,6H,J=6.8 Hz), 1.262–1.541(m,52H), 1.837–1.894(m,4H), 2.150(br.s,1H), 2.425(s,3H), 2.509(s,3H), 2.540–2.592(m,1H), 2.799(s,3H), 3.395(s,3H), 3.999(br.s,1H), 4.103(t,2H,J=6.6 Hz), 4.224(t, 2H,J=6.4 Hz), 4.835(br.s,1H), 5.170(d,2H,J=12.0 Hz), 6.685(br.s,1H), 7.061(dd,1H,J=2.4,9.0 Hz), 7.108–7.161(m, 2H), 7.287–7.595(m,7H), 9.080(s,1H).

Fab-MS(m/z);1095(M+1)⁺

Compound 39 was obtained from 211 mg (0.23 mmol) of the 11-Cbz derivative of Compound 39 and 70 mg of 10% Pd/C by the procedure analogous to that of Example 8 (yield: 126 mg, 67%).

¹HNMR(CDCl₃) δ; 0.879(t,6H,J=6.8 Hz), 1.204–1.570(m,52H), 1.612(br.s,3H), 1.817–1.907(m,4H), 2.308(s,3H), 2.363–2.409(m,1H), 2.685(dd,1H,J=3.9,14.9 Hz), 3.347(br.s,3H), 3.391(s,3H), 3.857(br.s,1H), 4.106(t, 2H,J=6.6 Hz), 4.227(t,2H,J=6.3 Hz), 4.915(d,2H,J=3.9 Hz), 6.495(d,1H,J=4.9 Hz), 7.035(dd,1H,J=2.7,9.3 Hz), 7.106(dd,1H,J=2.4,8.5 Hz), 7.154(d,1H,J=8.8 Hz), 7.327(d, 1H,J=2.7 Hz), 7.776(d,1H,J=9.3 Hz), 9.070(d,1H,J=2.4 Hz).

Fab-MS(m/z);961(M+1)⁺

Example 38

Compound 40

11-Cbz derivative of Compound 40 was obtained from 200 mg (0.31 mmol) of 2-methyl-11-Cbz-5,17-dihydroxystaurosporine, 37 mg (0.93 mmol) of 60% sodium hydride, and 296 μl (1.55 mmol) of 1-bromononane by the procedure analogous to that of Example 37 (yield: 278 mg, 72%).

¹HNMR(DMSO-d₆,70° C.) δ; 0.843–0.882(m,6H), 1.278–1.497(m,24H), 1.765–1.834(m,4H), 2.254(s,3H), 2.624(s,3H), 2.732(s,3H), 3.207(s,3H), 4.086(t,2H,J=6.5 Hz), 4.134(t,2H,J=6.4 Hz), 4.161(br.s,1H), 4.654(br.s,1H), 5.040(d,2H,J=2.2 Hz), 5.170(d,1H,J=12.5 Hz), 5.226(d,1H, J=12.2 Hz), 6.881(dd,1H,J=5.9,8.8 Hz), 7.075–7.108(m, 2H), 7.353–7.460(m,7H), 7.790(d,1H,J=8.8 Hz), 8.930(d, 1H,J=2.7 Hz)

Fab-MS(m/z);899(M+1)⁺

Compound 40 was obtained from 250 mg (0.23 mmol) of the resulting 11-Cbz derivative of Compound 40 and 100 mg of 10% Pd/C by the procedure analogous to that of Example 8 (yield: 182 mg, 80%).

¹HNMR(DMSO-d₆) δ; 0.850–0.884(m,6H), 1.224–1.514(m,24H), 1.769–1.838(m,4H), 2.005–2.079(m, 1H), 2.272(s,3H), 2.447(s,3H), 2.664(s,3H), 3.265(s,3H), 3.990(br.s,3H), 4.073(t,2H,J=6.6 Hz), 4.131(t,2H,J=6.7 Hz), 4.451(s,1H), 5.069(s,2H), 6.863(dd,1H,J=3.3,9.4 Hz), 7.114–7.155(m,2H), 7.446(d,1H,J=8.8 Hz), 7.468(d,1H,J=2.7 Hz), 7.947(d,1H,J=9.5 Hz), 8.940(d,1H,J=2.7 Hz), 8.965(br.s,1H), 9.170(br.s,1H)

Fab-MS(m/z); 765(M+1)$^+$

Example 39

Injections

Compound 22 (2.0 g) was dissolved in 20 l of ethanol, and the solution was subjected to pressure filtration through Millipore Filter (pore size: 0.22μ) for sterilization. The resulting sterile filtrate was put into brown vials in 5.0 ml portions, and lyophilized in a conventional manner to give 0.5 mg/vial of lyophilized preparations.

Example 40

Tablets

Tablets were prepared in a conventional manner using 180 mg of Compound 22, 90 mg of lactose, 40 mg of cornstarch, 4 mg of polyvinyl alcohol, 28 mg of Avicel and 1 mg of magnesium stearate.

Although the invention has been described in specific terms, it is to be understood that the described embodiments are only illustrative and various change and modifications may be imparted thereto without departing from the scope of the invention which is limited solely by the appended claims.

We claim:

1. An indolocarbazole derivative represented by the formula (I):

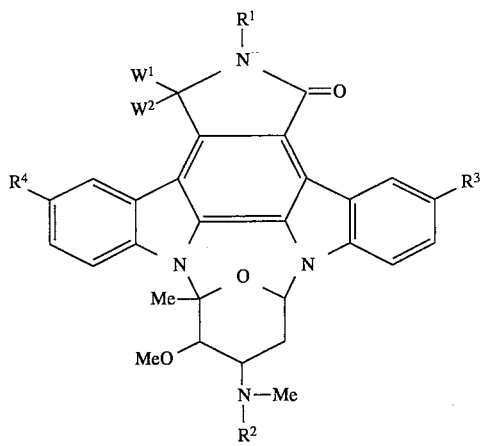

{wherein R$^1$ represents substituted or unsubstituted lower alkyl, R$^2$ represents hydrogen, substituted or unsubstituted lower alkyl, R$^3$ and R$^4$ are the same or different, and represent hydrogen, nitro, NR$^5$R$^6$ (wherein R$^5$ and R6 are the same or different and represent hydrogen, lower alkyl, an amino acid residue in which the hydroxy group is removed from the carboxylic acid, alkanoyl or CO(CH$_2$)$_m$NR$^7$R$^8$ wherein m is an integer of 0 to 3, R$^7$ and R$^8$ are the same or different and represent hydrogen or lower alkyl, or R$^7$ and R$^8$ are combined together with nitrogen atom to form a heterocyclic ring, OR$^9$ (wherein R$^9$ represents long-chain alkyl, alkanoyl, COCH$_2$(OCH$_2$CH$_2$)$_k$OCH$_3$ wherein k is an integer of 1 to 6, or CONR$^7$R$^8$, substituted or unsubstituted lower alkyl, substituted or unsubstituted lower alkenyl, or CH=NNR$^{10}$R$^{11}$ wherein R$^{10}$ and R$^{11}$ are the same or different and represent hydrogen, lower alkyl or a member selected from the group consisting of pyrrolyl, imidazolyl, thienyl, furyl, triazolyl, tetrazolyl, thiazolyl, oxazolyl, pyridyl, pyrimidinyl, indolyl and quinolyl, W$^1$ and W$^2$ are both hydrogen or are combined together to represent oxygen, and Me represents methyl, provided that when R$^1$ is unsubstituted lower alkyl, R$^3$ and R$^4$ are not simultaneously hydrogen}, or a pharmaceutically acceptable salt thereof.

2. A compound according to claim 1, in which R$^1$ is unsubstituted lower alkyl.

3. A compound according to claim 2, in which R$^1$ is methyl.

4. A compound according to any of claims 1–3, in which R$^2$ is hydrogen.

5. A compound according to any of claims 1–3, in which R$^3$ is NR$^5$R$^6$ (wherein R$^5$ and R$^6$ are the same or different and represent hydrogen, lower alkyl, an amino acid residue where hydroxy group in the carboxylic acid is removed from the amino acid, alkanoyl or CO(CH$_2$)$_m$NR$^7$R$^8$ (wherein m is an integer of 0 to 3, R$^7$ and R$^8$ are the same or different and represent hydrogen or lower alkyl, or R$^7$ and R$^8$ are combined together with nitrogen atom to form a heterocyclic ring)), OR$^9$(wherein R$^9$ represents long chain alkyl, alkanoyl, COCH$_2$(OCH$_2$CH$_2$)$_k$OCH$_3$ (wherein k is an integer of 1 to 6), or CONR$^7$R$^8$(wherein R$^7$ and R$^8$ have the same meanings as defined above)), substituted or unsubstituted lower alkyl, substituted or unsubstituted lower alkenyl, or CH=NNR$^{10}$R$^{11}$(wherein R$^{10}$ and R$^{11}$ are the same or different and represent hydrogen, lower alkyl or a heterocyclic ring containing nitrogen atom).

6. A compound according to any of claims 1–3, in which W represents two hydrogen atoms.

7. A pharmaceutical composition which comprises, as an active ingredient, a compound as defined by claim 1, and a pharmaceutically acceptable carrier.

8. A method of treating thrombocytopenia by administering, to a patient suffering from thrombocytopenia, an effective amount of the compound according to claim 1.

9. A compound according to claim 4, in which R$^3$ is NR$^5$R$^6$.

10. A compound according to claim 4, in which W represents two hydrogen atoms.

11. A compound according to claim 9, in which W represents two hydrogen atoms.

* * * * *

UNITED STATES PATENT AND TRADEMARK OFFICE
CERTIFICATE OF CORRECTION

PATENT NO. : 5,604,219
DATED : February 18, 1997
INVENTOR(S) : CHIKARA MURAKATA ET AL.

Page 1 of 5

It is certified that error appears in the above-identified patent and that said Letters Patent is hereby corrected as shown below:

COLUMN 2

Line 31, "long-chained" should read --long chain--.
  Line 51, "secbutyl," should read --sec-butyl,--.

COLUMN 3

Line 1, "long-chained" should read --long chain--.
  Line 28, "represents" should read --represent--.
  Line 34, "W" should read --$W^1$ and $W^2$--.
  Line 35, "preferably represents two hydrogen atoms" should read
    --each preferably represent a hydrogen atom--.

COLUMN 5

Line 25, "  $R^1$  " should read --  $R^1$  --.
           N                              |
          / \                             N
                                         / \

COLUMN 8

Line 2, "chained" should read --chain-- and
    "long-chained" should read --long chain--.

COLUMN 9

Line 56, "formula (VII):" should read --formula:--.

UNITED STATES PATENT AND TRADEMARK OFFICE
CERTIFICATE OF CORRECTION

PATENT NO. : 5,604,219
DATED : February 18, 1997
INVENTOR(S) : CHIKARA MURAKATA ET AL.

It is certified that error appears in the above-identified patent and that said Letters Patent is hereby corrected as shown below:

COLUMN 10

Line 19, "formula (VIII) or (IX);" should read --formulae:--.
Line 27, "$R^{12}$ and $R^{13}$" should read --$R^{12a}$ and $R^{13a}$--.
Line 58, "equivalents," should read --equivalents, respectively,--.

COLUMN 12

Line 6, "defined as" should read --as defined--.
Line 24, "THE" should read --THF--.

COLUMN 17

Line 40, "piper." should read --pipet.--.
Line 49, "37°C." should read --37°C.,--.

COLUMN 18

Line 22, "water)." should read --80/water).--.
Line 48, "a" should be deleted.
Line 63, "follows;" should read --follows:--.
Line 67, "W is" should read --$W^1$, $W^2$ are--.

COLUMN 19

Line 27, "0°C." should read --0°C.,--.

UNITED STATES PATENT AND TRADEMARK OFFICE
CERTIFICATE OF CORRECTION

PATENT NO. : 5,604,219
DATED : February 18, 1997
INVENTOR(S) : CHIKARA MURAKATA ET AL.

It is certified that error appears in the above-identified patent and that said Letters Patent is hereby corrected as shown below:

COLUMN 21

Line 48, "86%" should read --86%,--.

COLUMN 22

Line 57, "(83%" should read --(83%)--.

COLUMN 23

Line 24, "$^1$HNM-" should read --¶ $^1$HNM- --.
Line 41, "$^1$HNMR" should read --¶ $^1$HNMR--.
Line 47, "9,202(s,1H)" should read --9.202(s,1H)--.

COLUMN 25

Line 36, "evaporation,and" should read
--evaporation, and--.

COLUMN 27

Line 29, "68%)." should read --64%).--.

COLUMN 28

Line 52, "7 893" should read --7.893--.

UNITED STATES PATENT AND TRADEMARK OFFICE
CERTIFICATE OF CORRECTION

PATENT NO. : 5,604,219
DATED : February 18, 1997
INVENTOR(S) : CHIKARA MURAKATA ET AL.

It is certified that error appears in the above-identified patent and that said Letters Patent is hereby corrected as shown below:

COLUMN 29

Line 1, "9,0 Hz)," should read --9.0 Hz),--.
Line 12, "9,0 Hz)," should read --9.0 Hz),--.

COLUMN 30

Line 33, "$\mu$(1.2 mmol)" should read --$\mu$l(1.2 mmol)--.

COLUMN 32

Line 27, "(0.118 mmol" should read --(0.118 mmol)--.

COLUMN 34

Line 36, "$^1$HNMR" should read --¶ $^1$HNMR--.

COLUMN 37

Line 24, "change" should read --changes--.
Line 51, "R6" should read --$R^6$--.

UNITED STATES PATENT AND TRADEMARK OFFICE
CERTIFICATE OF CORRECTION

PATENT NO. : 5,604,219
DATED : February 18, 1997
INVENTOR(S) : CHIKARA MURAKATA ET AL.

It is certified that error appears in the above-identified patent and that said Letters Patent is hereby corrected as shown below:

COLUMN 38

Line 39, "W represents two hydrogen atoms." should read --$W^1$ and $W^2$ each represents a hydrogen atom.--.

Line 48, "W represents two hydrogen atoms." should read --$W^1$ and $W^2$ each represents a hydrogen atom.--.

Line 50, "W represents two hydrogen atoms." should read --$W^1$ and $W^2$ each represents a hydrogen atom.--.

Signed and Sealed this

Fourth Day of November, 1997

Attest:

BRUCE LEHMAN

Attesting Officer

Commissioner of Patents and Trademarks